(12) United States Patent
Oh et al.

(10) Patent No.: US 12,188,947 B2
(45) Date of Patent: Jan. 7, 2025

(54) MARKER FOR DIAGNOSING ATHEROSCLEROSIS SEVERITY, AND DIAGNOSTIC METHOD USING SAME

(71) Applicant: EWHA UNIVERSITY—INDUSTRY COLLABORATION FOUNDATION, Seoul (KR)

(72) Inventors: Goo Taeg Oh, Seoul (KR); Sejin Jeon, Seoul (KR); Tae Kyeong Kim, Seoul (KR); Yangsoo Jang, Seoul (KR); Sung-Jin Hong, Seoul (KR); Hye-Young Yun, Seoul (KR)

(73) Assignee: EWHA UNIVERSITY—INDUSTRY COLLABORATION FOUNDATION, Seoul (KR)

( * ) Notice: Subject to any disclaimer, the term of this patent is extended or adjusted under 35 U.S.C. 154(b) by 727 days.

(21) Appl. No.: 17/293,946

(22) PCT Filed: Nov. 5, 2019

(86) PCT No.: PCT/KR2019/014931
§ 371 (c)(1),
(2) Date: May 14, 2021

(87) PCT Pub. No.: WO2020/101251
PCT Pub. Date: May 22, 2020

(65) Prior Publication Data
US 2022/0026443 A1    Jan. 27, 2022

(30) Foreign Application Priority Data

Nov. 14, 2018   (KR) .................. 10-2018-0140320
Nov. 5, 2019    (KR) .................. 10-2019-0140180

(51) Int. Cl.
*G01N 33/68*   (2006.01)
*A61K 38/17*   (2006.01)
*A61P 9/10*    (2006.01)

(52) U.S. Cl.
CPC ..... *G01N 33/6893* (2013.01); *A61K 38/1709* (2013.01); *A61P 9/10* (2018.01); *G01N 2800/2871* (2013.01); *G01N 2800/323* (2013.01); *G01N 2800/324* (2013.01); *G01N 2800/56* (2013.01)

(58) Field of Classification Search
CPC ....... G01N 33/6893; G01N 2800/2871; G01N 2800/323; G01N 2800/324; G01N 2800/56; A61K 38/1709; A61P 9/10
See application file for complete search history.

(56) References Cited

U.S. PATENT DOCUMENTS

2006/0127894 A1*  6/2006  Azimzai .................. A61P 29/00
                                                       435/7.1
2011/0065199 A1   3/2011  Kuge et al.
2017/0343547 A1   11/2017 Nakamura et al.

FOREIGN PATENT DOCUMENTS

KR    10-2017-0107934 A    9/2017
KR    10-2017-0141993 A    12/2017

OTHER PUBLICATIONS

Uniprotkb Q8N145 accessed Oct. 28, 2023 at URL uniprot.org/uniprotkb/Q8N145.txt, pp. 1-6 (2023) (Year: 2023).*
Tolle et al., "Arteriosclerosis and vascular calcification: causes, clinical assessment and therapy," European Journal of Clinical Investigation 45:895-1003 (2015) (Year: 2015).*
Kim et al., "Leucine-rich glioma inactivated 3 associates negatively with adiponectin," Cytokine 62:206-209 (2013) (Year: 2013).*
Kim et al., "Leucine-rich glioma inactivated 3: Integrative analyses support its role in the cytokine network," Int'l J. Mol. Med. 40:251-259 (2017) (Year: 2017).*
Park, Woo-Jae, et al., "Leucine-Rich Glioma Inactivated 3 Induces Neurite Outgrowth Through Akt and Focal Adhesion Kinase", Neurochem Res, 2010, 35: 789-796.
"Effects of Pitavastatin Treatments on the Plasma Lgi3 Level in the Patients with Dyslipidemia", ClinicalTrials.gov, 2018.
Japanese Office Action for Application No. 2021-526307, Sent Nov. 29, 2022, 7 Pages.
NCBI, Accession No. NP_644807, leucine-rich repeat LGI family membor 3 precursor [Homo sapiens], 2018. 3 pages.
Park, W.-J., "Leucine-rich glioma inactivated 3 induces neurite outgrowth through Akt and focal adhesion kinase", Neurochem. Res., (20100000), vol. 35, 13 pages, XP019793679.

* cited by examiner

*Primary Examiner* — Julie Ha
*Assistant Examiner* — Kristina M Hellman
(74) *Attorney, Agent, or Firm* — Riverside Law LLP

(57) ABSTRACT

The present invention pertains to: a marker composition for diagnosing atherosclerosis severity; a composition for diagnosing atherosclerosis severity; an atherosclerosis severity diagnosis kit including the composition; a method for screening substances for preventing or treating atherosclerosis; and a method for providing information about a diagnosis of atherosclerosis severity, wherein LGI3 expression or activity levels are used. According to the present invention, the severity of atherosclerosis can be diagnosed or predicted, and personalized medicine and predictive medicine can be practiced using such information. Moreover, the present invention can treat atherosclerosis without affecting other metabolic phenotypes by administering an LGI3 antagonist.

6 Claims, 9 Drawing Sheets

Specification includes a Sequence Listing.

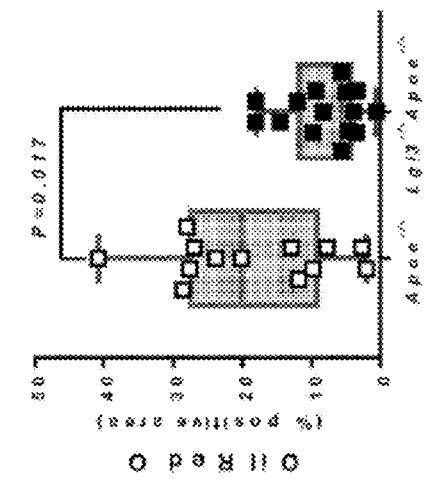
Fig. 1B
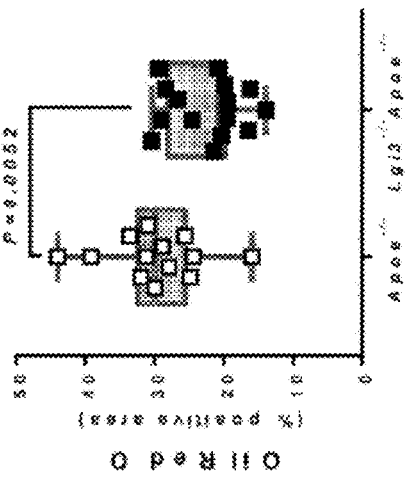
Fig. 1C
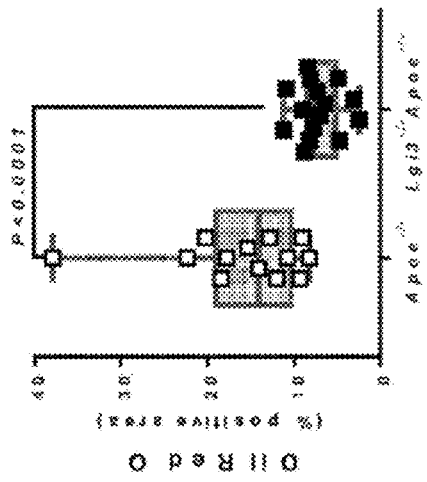
Fig. 1D
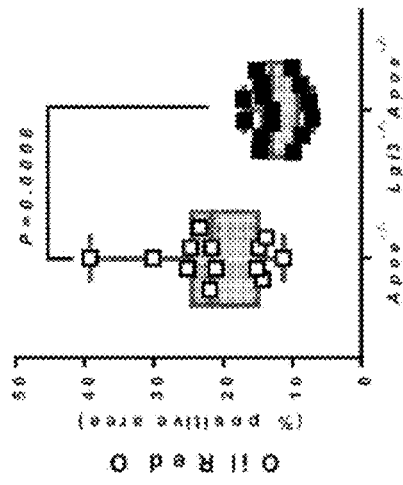
Fig. 1E
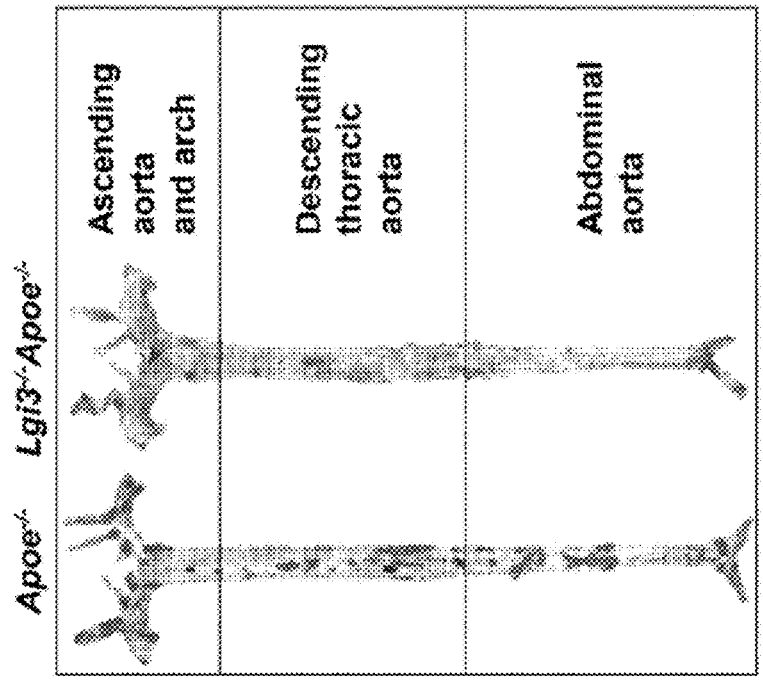
Fig. 1A
Fig. 1

Apoe-/- + PBS    Apoe-/- + LGl3 p34

Ascending aorta and arch
Descending thoracic aorta
Abdominal aorta

Fig. 5B — Total Aorta; Oil Red O (%positive area); p= 0.042; LGl3 p34 − / +

Fig. 5C — Ascending aorta and arch; Oil Red O (%positive area); p= 0.4487; LGl3 p34 − / +

Fig. 5D — Descending thoracic aorta; Oil Red O (%positive area); p= 0.0064; LGl3 p34 − / +

Fig. 5E — Abdominal aorta; Oil Red O (%positive area); p= 0.0558; LGl3 p34 − / +

Fig. 5

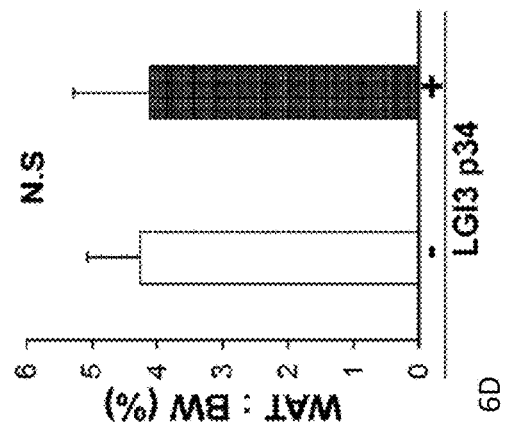
Fig. 6A
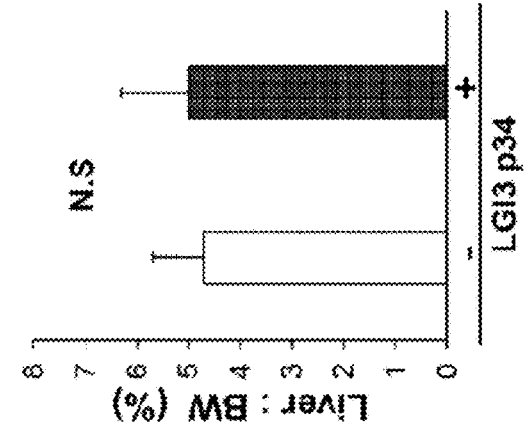
Fig. 6B
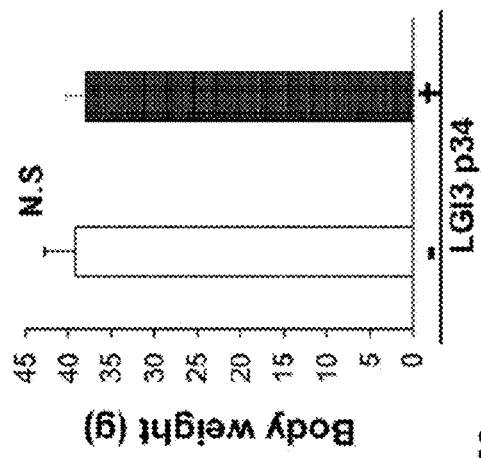
Fig. 6C
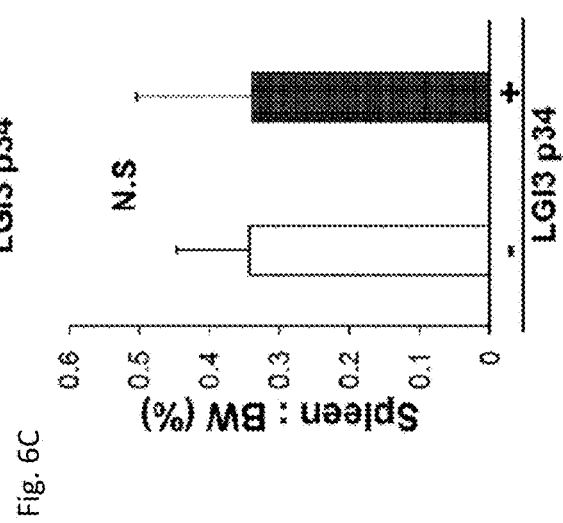
Fig. 6D
Fig. 6

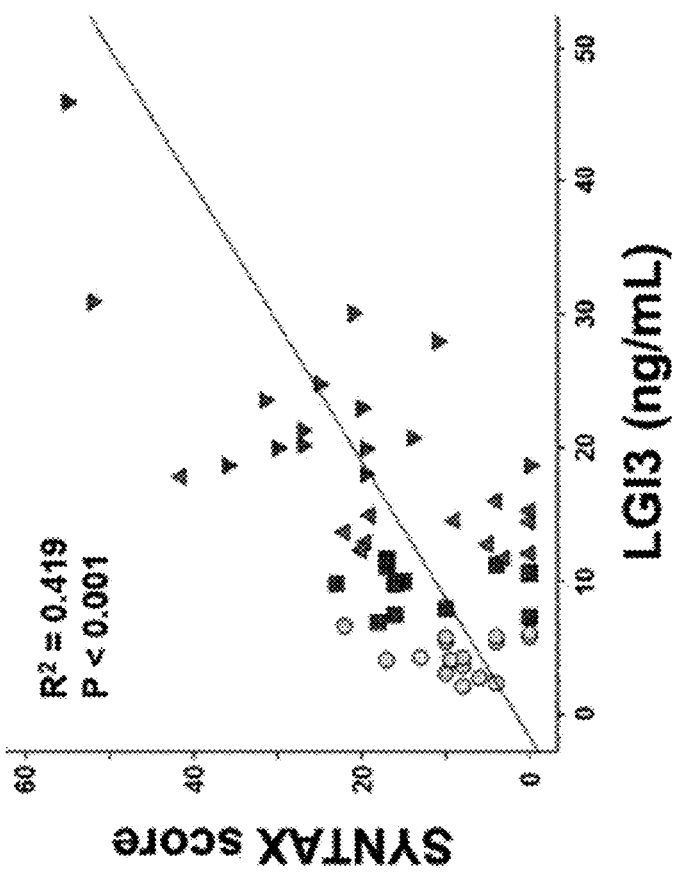
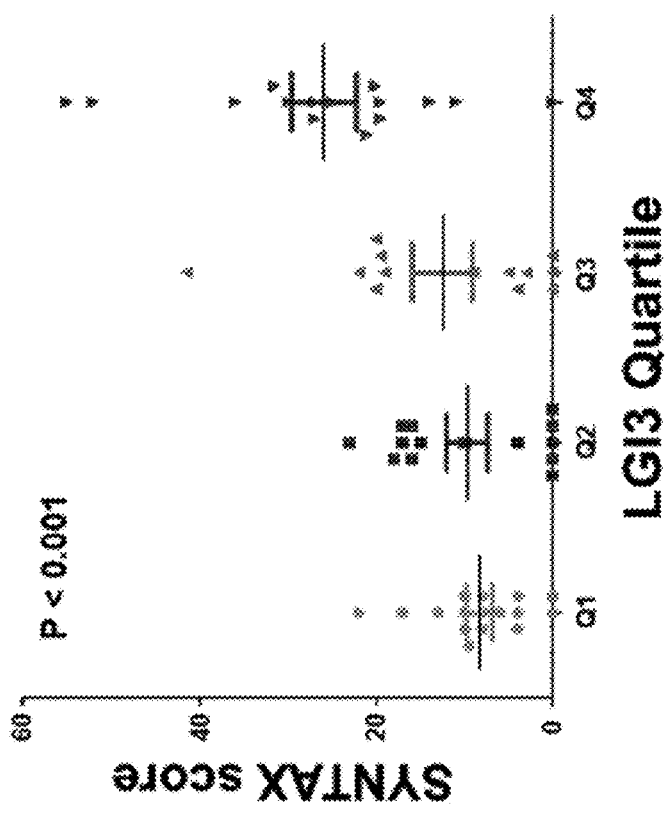
Fig. 7A
Fig. 7B
Fig. 7

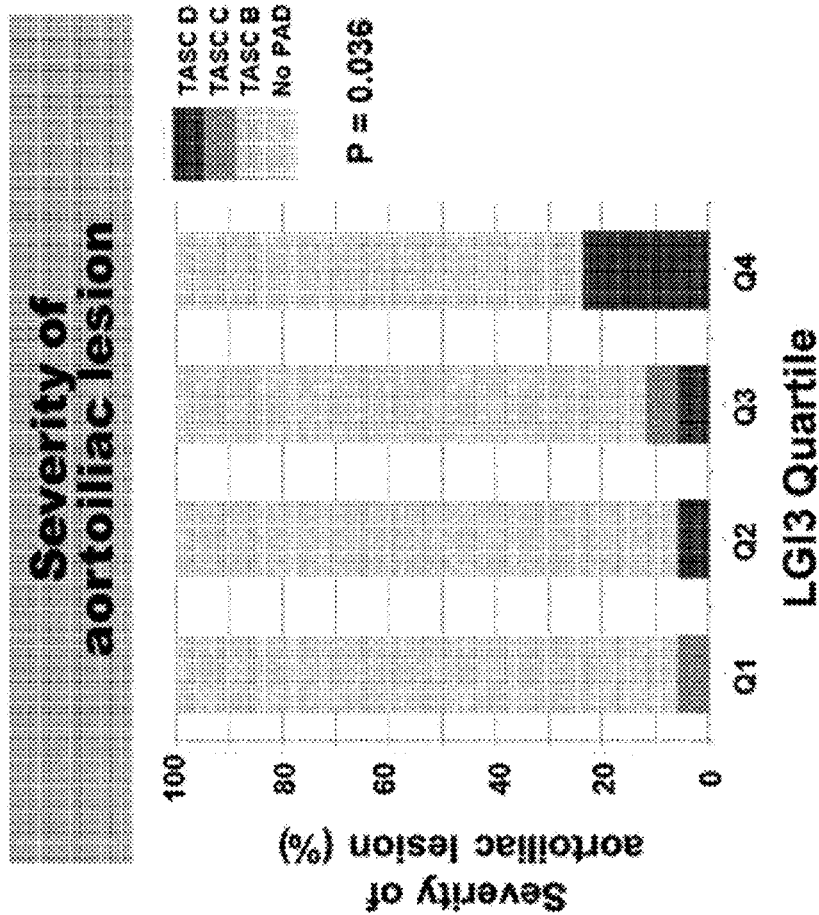
Fig. 8B
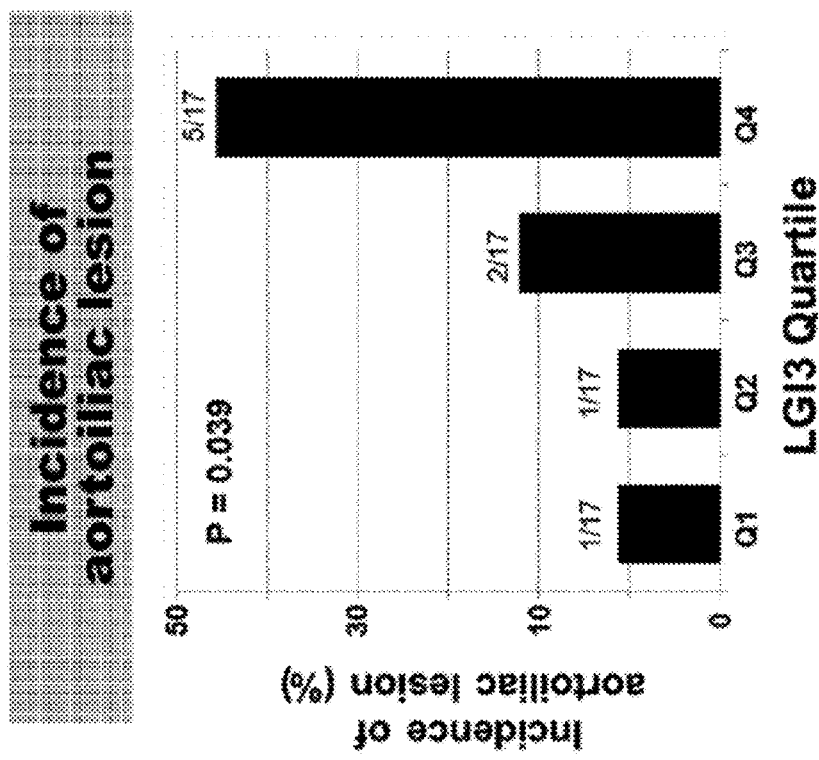
Fig. 8A
Fig. 8

SEQUENCE LISTING

<160> NUMBER OF SEQ ID NOS: 3

<210> SEQ ID NO 1
<211> LENGTH: 548
<212> TYPE: PRT
<213> ORGANISM: Homo sapiens

<400> SEQUENCE: 1

```
Met Ala Gly Leu Arg Ala Arg Gly Gly Pro Gly Pro Gly Leu Leu Ala
1               5                   10                  15

Leu Ser Ala Leu Gly Phe Cys Leu Met Leu Gln Val Ser Ala Lys Arg
                20                  25                  30

Pro Pro Lys Thr Pro Pro Cys Pro Pro Ser Cys Ser Cys Thr Arg Asp
            35                  40                  45

Thr Ala Phe Cys Val Asp Ser Lys Ala Val Pro Arg Asn Leu Pro Ser
        50                  55                  60

Glu Val Ile Ser Leu Thr Leu Val Asn Ala Ala Phe Ser Glu Ile Gln
65                  70                  75                  80

Asp Gly Ala Phe Ser His Leu Pro Leu Leu Gln Phe Leu Leu Leu Asn
                85                  90                  95
```

```
Ser Asn Lys Phe Thr Leu Ile Gly Asp Asn Ala Phe Thr Gly Leu Ser
            100                 105                 110

His Leu Gln Tyr Leu Phe Ile Glu Asn Asn Asp Ile Trp Ala Leu Ser
            115                 120                 125

Lys Phe Thr Phe Arg Gly Leu Lys Ser Leu Thr His Leu Ser Leu Ala
    130                 135                 140

Asn Asn Asn Leu Gln Thr Leu Pro Arg Asp Ile Phe Arg Pro Leu Asp
145                 150                 155                 160

Ile Leu Asn Asp Leu Asp Leu Arg Gly Asn Ser Leu Asn Cys Asp Cys
                165                 170                 175

Lys Val Lys Trp Leu Val Glu Trp Leu Ala His Thr Asn Thr Thr Val
            180                 185                 190

Ala Pro Ile Tyr Cys Ala Ser Pro Arg Phe Gln Glu His Lys Val
        195                 200                 205

Gln Asp Leu Pro Leu Arg Glu Phe Asp Cys Ile Thr Thr Asp Phe Val
    210                 215                 220

Leu Tyr Gln Thr Leu Ala Phe Pro Ala Val Ser Ala Glu Pro Phe Leu
225                 230                 235                 240

Tyr Ser Ser Asp Leu Tyr Leu Ala Leu Ala Gln Pro Gly Val Ser Ala
                245                 250                 255

Cys Thr Ile Leu Lys Trp Asp Tyr Val Glu Arg Gln Leu Arg Asp Tyr
            260                 265                 270

Asp Arg Ile Pro Ala Pro Ser Ala Val His Cys Lys Pro Met Val Val
        275                 280                 285

Asp Ser Gln Leu Tyr Val Val Ala Gln Leu Phe Gly Gly Ser Tyr
    290                 295                 300

Ile Tyr His Trp Asp Pro Asn Thr Thr Arg Phe Thr Arg Leu Gln Asp
305                 310                 315                 320

Ile Asp Pro Gln Arg Val Arg Lys Pro Asn Asp Leu Glu Ala Phe Arg
                325                 330                 335

Ile Asp Gly Asp Trp Tyr Phe Ala Val Ala Asp Ser Ser Lys Ala Gly
            340                 345                 350

Ala Thr Ser Leu Tyr Arg Trp His Gln Asn Gly Phe Tyr Ser His Gln
        355                 360                 365

Ala Leu His Pro Trp His Arg Asp Thr Asp Leu Glu Phe Val Asp Gly
    370                 375                 380

Glu Gly Lys Pro Arg Leu Ile Val Ser Ser Ser Gln Ala Pro Val
385                 390                 395                 400

Ile Tyr Gln Trp Ser Arg Thr Gln Lys Gln Phe Val Ala Gln Gly Glu
                405                 410                 415

Val Thr Gly Val Pro Asp Ala Gln Ala Val Lys His Phe Arg Ala Gly
            420                 425                 430

Arg Asp Ser Tyr Leu Cys Leu Ser Arg Tyr Ile Gly Asp Ser Lys Ile
        435                 440                 445

Leu Arg Trp Glu Gly Thr Arg Phe Ser Glu Val Gln Ala Leu Pro Ser
    450                 455                 460

Arg Gly Ser Leu Ala Leu Gln Pro Phe Leu Val Gly Gly Arg Arg Tyr
465                 470                 475                 480

Leu Ala Leu Gly Ser Asp Phe Ser Phe Thr Gln Ile Tyr Gln Trp Asp
                485                 490                 495

Glu Gly Arg Gln Lys Phe Val Arg Phe Gln Glu Leu Ala Val Gln Ala
            500                 505                 510
```

```
Pro Arg Ala Phe Cys Tyr Met Pro Ala Gly Asp Ala Gln Leu Leu Leu
            515                 520                 525
Ala Pro Ser Phe Lys Gly Gln Thr Leu Val Tyr Arg His Ile Val Val
530                 535                 540
Asp Leu Ser Ala
545

<210> SEQ ID NO 2
<211> LENGTH: 548
<212> TYPE: PRT
<213> ORGANISM: Mus musculus

<400> SEQUENCE: 2

Met Ala Gly Leu Arg Ala Arg Arg Gly Pro Gly Arg Arg Leu Leu Val
1               5                   10                  15
Leu Ser Thr Leu Gly Phe Cys Leu Met Leu Gln Val Ser Ala Lys Arg
                20                  25                  30
Pro Pro Lys Thr Pro Pro Cys Pro Ser Cys Ser Cys Thr Arg Asp
            35                  40                  45
Thr Ala Phe Cys Val Asp Ser Lys Ser Val Pro Lys Asn Leu Pro Ser
    50                  55                  60
Glu Val Ile Ser Leu Thr Leu Val Asn Ala Ala Phe Ser Glu Ile Gln
65                  70                  75                  80
Asp Gly Ala Phe Ser His Leu Pro Leu Leu Gln Phe Leu Leu Leu Asn
                85                  90                  95
Ser Asn Lys Phe Thr Leu Ile Gly Asp Asn Ala Phe Ile Gly Leu Ser
            100                 105                 110
His Leu Gln Tyr Leu Phe Ile Glu Asn Asn Asp Ile Trp Ala Leu Ser
        115                 120                 125
Lys Phe Thr Phe Arg Gly Leu Lys Ser Leu Thr His Leu Ser Leu Ala
    130                 135                 140
Asn Asn Asn Leu Gln Thr Leu Pro Arg Asp Ile Phe Arg Pro Leu Asp
145                 150                 155                 160
Ile Leu Ser Asp Leu Asp Leu Arg Gly Asn Ala Leu Asn Cys Asp Cys
                165                 170                 175
Lys Val Lys Trp Leu Val Glu Trp Leu Ala His Thr Asn Thr Thr Val
            180                 185                 190
Ala Pro Ile Tyr Cys Ala Ser Pro Pro Arg Phe Gln Glu His Lys Val
        195                 200                 205
Gln Asp Leu Pro Leu Arg Glu Phe Asp Cys Ile Thr Thr Asp Phe Val
    210                 215                 220
Leu Tyr Gln Thr Leu Ser Phe Pro Ala Val Ser Ala Glu Pro Phe Leu
225                 230                 235                 240
Tyr Ser Ser Asp Leu Tyr Leu Ala Leu Ala Gln Pro Gly Ala Ser Ala
                245                 250                 255
Cys Thr Ile Leu Lys Trp Asp Tyr Val Glu Arg Gln Leu Arg Asp Tyr
            260                 265                 270
Asp Arg Ile Pro Ala Pro Ser Ala Val His Cys Lys Pro Met Val Val
        275                 280                 285
Asp Gly Gln Leu Tyr Val Val Ala Gln Leu Phe Gly Gly Ser Tyr
    290                 295                 300
Ile Tyr His Trp Asp Pro Asn Thr Thr Arg Phe Thr Lys Leu Gln Asp
305                 310                 315                 320
Ile Asp Pro Gln Arg Val Arg Lys Pro Asn Asp Leu Glu Ala Phe Arg
                325                 330                 335
```

```
Ile Asp Gly Asp Trp Phe Phe Ala Val Ala Asp Ser Ser Lys Ala Gly
            340             345             350

Ala Thr Ser Leu Tyr Arg Trp His Gln Asn Gly Phe Tyr Ser His Gln
            355             360             365

Ala Leu His Ala Trp His Arg Asp Thr Asp Leu Glu Phe Val Asp Gly
            370             375             380

Glu Gly Lys Pro Arg Leu Ile Val Ser Ser Ser Gln Ala Pro Val
385             390             395             400

Ile Tyr Gln Trp Ser Arg Ser Gln Lys Gln Phe Val Ala Gln Gly Glu
            405             410             415

Val Thr Gln Val Pro Asp Ala Gln Ala Val Lys His Phe Arg Ala Gly
            420             425             430

Arg Asp Ser Tyr Leu Cys Leu Ser Arg Tyr Ile Gly Asp Ser Lys Ile
            435             440             445

Leu Arg Trp Glu Gly Thr Arg Phe Ser Glu Val Gln Ala Leu Pro Ser
450             455             460

Arg Gly Ser Leu Ala Leu Gln Pro Phe Leu Val Gly Gly His Arg Tyr
465             470             475             480

Leu Ala Leu Gly Ser Asp Phe Ser Phe Thr Gln Ile Tyr Gln Trp Asp
            485             490             495

Glu Gly Arg Gln Lys Phe Val Arg Phe Gln Glu Leu Ala Val Gln Ala
            500             505             510

Pro Arg Ala Phe Cys Tyr Met Pro Ala Gly Asp Ala Gln Leu Leu Leu
            515             520             525

Ala Pro Ser Phe Lys Gly Gln Thr Leu Val Tyr Arg His Val Val Val
            530             535             540

Asp Leu Ser Ala
545

<210> SEQ ID NO 3
<211> LENGTH: 15
<212> TYPE: PRT
<213> ORGANISM: Homo sapiens

<400> SEQUENCE: 3

Asp Glu Gly Arg Gln Lys Phe Val Arg Phe Gln Glu Leu Ala Val
1               5                   10                  15
```

MARKER FOR DIAGNOSING ATHEROSCLEROSIS SEVERITY, AND DIAGNOSTIC METHOD USING SAME

CROSS-REFERENCE TO RELATED APPLICATIONS

This application is the U.S. national phase application filed under 35 U.S.C. § 371 claiming benefit to International Patent Application No. PCT/KR2019/014931, filed Nov. 5, 2019, which is entitled to priority of Korean Patent Application No. 10-2019-0140180, filed on Nov. 5, 2019, and Korean Patent Application No. 10-2018-0140320 filed on Nov. 14, 2018, the contents of each of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0116-00US Sequence Listing.txt" in ASCII format. The text file containing the Sequence Listing of the present application was created on May 7, 2021 and is 10,376 bytes in size.

TECHNICAL FIELD

The present invention relates a marker composition for diagnosing arteriosclerosis severity, a composition for diagnosing arteriosclerosis severity, a kit for diagnosing arteriosclerosis severity including the composition, a method of screening a substance for preventing or treating arteriosclerosis, and a method of providing information about a diagnosis of atherosclerosis severity.

This application claims priority to and the benefit of Korean Patent Application No. 10-2018-0140320 filed on Nov. 14, 2018 and Korean Patent Application No. 10-2019-0140180 filed on Nov. 5, 2019, and all contents disclosed in the specification and drawings of the application are incorporated herein by reference.

BACKGROUND ART

Arteriosclerosis refers to a vascular disease in which cholesterol accumulates on the endothelium, which mainly covers the innermost part of blood vessels, and proliferation of endothelial cells occurs, resulting in the formation of an "atheroma". It progresses slowly over a long period of time and occurs frequently in the coronary arteries, the carotid arteries, the lower abdominal aorta, the popliteal artery, and the like, and depending on the site of occurrence, it can cause fatal diseases such as angina pectoris, cerebral infarction, cerebral hemorrhage, kidney failure, ischemic limb disease, stroke, myocardial infarction, and the like.

Depending on the arteriosclerosis severity, blood vessels are narrowed and blocked, resulting in blood circulation disorders in the area responsible for the blood vessels, and symptoms are caused by narrowed blood vessels. It is known that the more risk factors there are, the faster the progression of arteriosclerosis occurs. The main risk factors are hypercholesterolemia, lack of HDL cholesterol, excess LDL cholesterol, high triglycerides, high blood pressure, smoking, diabetes, family history of cardiovascular disease, aging, lack of exercise, overweight, abdominal obesity, and the like. However, since the main risk factors and the arteriosclerosis severity are not proportional, there is a difficulty in that the arteriosclerosis severity cannot be determined only by checking the main risk factors.

The arteriosclerosis severity is an important factor in determining the treatment method (e.g., surgical procedure, etc.). Moreover, according to the severity, a major adverse cardiac and cerebrovascular event (MACCE)-free survival rate is determined, and the likelihood of very dangerous clinical symptoms such as stroke or myocardial infarction rapidly increases. Therefore, it is essential to diagnose the arteriosclerosis severity. As part of a method of diagnosing the arteriosclerosis severity, there is a method to check the degree of coronary artery stenosis. However, since the severity and symptoms of coronary artery stenosis are not consistent, the limitations of coronary angiography have been raised in evaluating the early detection of slowly progressive coronary artery disease, epidemiologic investigation, or reduction of coronary atherosclerosis according to risk factor control, etc.

Accordingly, there is an emerging need for developing a method of confirming arteriosclerosis, and further accurately diagnosing the arteriosclerosis severity.

Meanwhile, LGI3 (leucine rich repeat LGI family member 3 or leucine rich glioma inactivated 3) is a secreted protein that is present only in vertebrates including humans and functions thereof such as regulation of secretion and differentiation in neurons, regulation of survival and migration of skin keratinocytes, regulation of pigment production of melanocytes, differentiation of adipocytes, and inflammation of obese fat tissue are known. The LGI3 gene is located on human chromosome 8p21.3 (Gene ID: 203190), the number of exons is 8, and consists of 548 amino acids (NCBI Reference Sequence: NP_644807, SEQ ID NO: 1). In addition, the LGI3 cDNA cloned from the brain cDNA library of a mouse (Mus musculus) is composed of 2,931 nucleotides, and like humans, it is also composed of 548 amino acids (NCBI Reference Sequence: NP_660254.1, SEQ ID NO: 2).

However, according to studies on LGI3 to date, it is unknown whether the expression or activity level of LGI3 is increased in proportion to the arteriosclerosis severity.

DISCLOSURE

Technical Problem

The present invention provides, using an expression or activity level of LGI3, a marker composition for diagnosing arteriosclerosis severity, a composition for diagnosing arteriosclerosis severity, a kit for diagnosing arteriosclerosis severity including the composition, a method of screening a substance for preventing or treating arteriosclerosis, and a method of providing information about a diagnosis of atherosclerosis severity.

However, the technical task to be achieved by the present invention is not limited to the tasks mentioned above, and other tasks that are not mentioned can be clearly understood by those of ordinary skill in the technical field to which the present invention belongs from the following description.

Technical Solution

In order to achieve the above objective, the present invention provides a method of providing information for diagnosis of arteriosclerosis severity, including the steps of (a) checking an expression or activity level of leucine rich repeat LGI family member 3 (LGI3) represented by the amino acid sequence of SEQ ID NO: 1 or SEQ ID NO: 3 in a sample; and (b) when the expression or activity level in the step (a) is increased compared to the expression or activity level of LGI3 represented by the amino acid sequence of SEQ ID NO: 1 or SEQ ID NO: 3 in a control group, diagnosing the arteriosclerosis severity as severe.

As an embodiment of the present invention, the arteriosclerosis may be coronary artery disease or peripheral artery disease.

As an embodiment of the present invention, the control group may be samples collected at different times from patients who collected the sample in the step (a).

As another embodiment of the present invention, the information-providing method provides a method characterized by diagnosing a major adverse cardiac and cerebrovascular event (MACCE)-free survival rate along with the arteriosclerosis severity.

Here, when the expression or activity level of LGI3 represented by the amino acid sequence of SEQ ID NO: 1 or SEQ ID NO: 3 is increased compared to the expression or activity level of LGI3 represented by the amino acid sequence of SEQ ID NO: 1 or SEQ ID NO: 3 in the control, a low major adverse cardiac and cerebrovascular event (MACCE)-free survival rate is diagnosed.

As another embodiment of the present invention, the major adverse cardiac and cerebrovascular event may be myocardial infarction or stroke.

As another embodiment of the present invention, for the diagnosis of the severity of the coronary artery disease, the information-providing method may replace or may be used in parallel with the Synergy between PCI with Taxus and Cardiac Surgery (SYNTAX).

As another embodiment of the present invention, for the diagnosis of the severity of the peripheral arterial disease, the information-providing method may replace or may be used in parallel with Trans-Atlantic Inter-Society Consensus (TASC).

In addition, the present invention provides a biomarker composition for diagnosing atherosclerosis severity, including LGI3 represented by the amino acid sequence of SEQ ID NO: 1 or SEQ ID NO: 3.

In addition, the present invention provides a biomarker composition for diagnosing arteriosclerosis severity, including an agent for measuring an expression or activity level of LGI3 represented by the amino acid sequence of SEQ ID NO: 1 or SEQ ID NO: 3.

In addition, the present invention provides a kit for diagnosing arteriosclerosis severity, including the composition.

In addition, the present invention provides a method of screening a substance for preventing or treating arteriosclerosis, including the steps of (a) checking an expression or activity level of leucine rich repeat LGI family member 3 (LGI3) represented by the amino acid sequence of SEQ ID NO: 1 or SEQ ID NO: 3 after treatment with a candidate substance; and (b) when the expression or activity level in the step (a) is lowered, selecting the candidate substance as a material for preventing or treating arteriosclerosis.

In addition, the present invention provides a use for preventing and/or treating arteriosclerosis including an LGI3 antagonist represented by the amino acid sequence of SEQ ID NO: 3 as an active ingredient.

More specifically, the present invention provides a pharmaceutical composition for preventing or treating arteriosclerosis including an LGI3 antagonist represented by the amino acid sequence of SEQ ID NO: 3 as an active ingredient. In addition, the present invention provides a method of treating arteriosclerosis by administering an effective amount of an LGI3 antagonist represented by the amino acid sequence of SEQ ID NO: 3 to a patient with arteriosclerosis. In addition, the present invention provides a use of the LGI3 antagonist represented by the amino acid sequence of SEQ ID NO: 3 to treat or prevent arteriosclerosis.

Advantageous Effects

According to the present invention, it is possible to diagnose the arteriosclerosis severity accurately and conveniently just by checking the expression or activity level of LGI3. This can be used as an important index to comprehend the condition (whether the patient will improve or recurrence, etc.) of a patient with arteriosclerosis and to determine the appropriateness of the current treatment method, thereby realizing customized or predictive medicine. In addition, according to the present invention, it is possible to develop a therapeutic substance for improving the arteriosclerosis severity, and the present invention is expected to provide a platform for using these therapeutic substances in various ways, such as pharmaceutical, external, and food additive compositions. Furthermore, according to the present invention, since it does not affect the metabolic phenotype, it is expected that atherosclerosis treatment is possible without side effects.

DESCRIPTION OF DRAWINGS

FIG. 1, comprising FIG. 1A through FIG. 1E, shows that LGI3 deficiency reduces atherosclerotic plaque formation. FIG. 1A shows a representative image of atherosclerotic plaque formation in the aorta of Apoe$^{-/-}$ and Lgi3$^{-/-}$ Apoe$^{-/-}$ mice. FIG. 1B shows quantification of atherosclerotic plaque formation of the total aorta shown in FIG. 1A. FIG. 1C shows quantification of atherosclerotic plaque formation of the ascending aorta and arch shown in FIG. 1A. FIG. 1D shows quantification of atherosclerotic plaque formation of the descending thoracic aorta shown in FIG. 1A. FIG. 1E shows quantification of atherosclerotic plaque formation of the abdominal aorta shown in FIG. 1A.

FIG. 2A and FIG. 2B, shows that LGI3 deficiency reduces the formation of lesions in the aortic sinus. FIG. 2A shows representative images of lesions in the aortic sinus of Apoe$^{-/-}$ and Lgi3$^{-/-}$ Apoe$^{-/-}$ mice. FIG. 2B shows quantification of the lesions in the aortic sinus shown in FIG. 2A.

FIG. 3A through FIG. 3E, shows that body weight increase is reduced and weight of inguinal white fat is reduced due to LGI3 deficiency. FIG. 3A depicts representative body weight over time for Apoe$^{-/-}$ mice (white) and Lgi3$^{-/-}$ Apoe$^{-/-}$ mice (black). FIG. 3B depicts representative bodyweight increase over time in Apoe$^{-/-}$ mice and Lgi3$^{-/-}$ Apoe$^{-/-}$ mice. FIG. 3C depicts representative white adipose tissue (WAT) to body weight (BW) in Apoe$^{-/-}$ mice and Lgi3$^{-/-}$ Apoe$^{-/-}$ mice. FIG. 3D depicts representative liver weight to body weight in Apoe$^{-/-}$ mice and Lgi3$^{-/-}$ Apoe$^{-/-}$ mice. FIG. 3E depicts representative spleen weight to body weight in Apoe$^{-/-}$ mice and Lgi3$^{-/-}$ Apoe$^{-/-}$ mice.

FIG. 4A and FIG. 4B, shows an increase in LGI3 in plasma of a mouse model of atherosclerosis. FIG. 4A depicts representative LGI3 plasma levels in Apoe$^{-/-}$ mice at 8 weeks and 13 weeks, where the mice were fed a normal diet (NCD) for the first eight weeks and then transition to a high fat died (WD). FIG. 4B depicts representative LGI3 plasma levels in Apoe$^{-/-}$ mice fed a normal diet for 8 weeks followed by a high fat diet thereafter.

FIG. 5, comprising FIG. 5A through FIG. 5E, shows that LGI3 antagonist (LGI3 p34) reduces atherosclerotic plaque formation in Apoe$^{-/-}$ mice. FIG. 5A depicts representative images of atherosclerotic plaque formation in the aorta of Apoe$^{-/-}$ control mice (PBS) or treated with LGI3 p34. FIG. 5B shows quantification of atherosclerotic plaque formation of the total aorta shown in FIG. 5A. FIG. 5C shows quantification of atherosclerotic plaque formation of the ascending aorta and arch shown in FIG. 5A. FIG. 5D shows quantification of atherosclerotic plaque formation of the descending thoracic aorta shown in FIG. 5A. FIG. 5E shows quantification of atherosclerotic plaque formation of the abdominal aorta shown in FIG. 5A.

FIG. 6, comprising FIG. 6A through FIG. 6D, shows that the metabolic phenotype is not changed by treatment with an LGI3 antagonist (LGI3 p34). FIG. 6A depicts representative body weight in control mice compared to mice treated with LGI3 p34. FIG. 6B depicts representative WAT to body weight in control mice compared to mice treated with LGI3 p34. FIG. 6C depicts representative spleen weight to body weight in control mice compared to mice treated with LGI3 p34. FIG. 6D depicts representative liver weight to body weight in control mice compared to mice treated with LGI3 p34.

FIG. 7, comprising FIG. 7A and FIG. 7B, shows the relationship between the expression level of LGI3 and coronary artery disease (CAD). FIG. 7A depicts representative patient SYNTAX score for the four quartiles of LGI3 concentration in the corresponding patient samples. FIG. 7B depicts a representative correlation between patient SYNTAX score and LGI3 concentration in the corresponding patient samples.

FIG. 8, comprising FIG. 8A and FIG. 8B, shows the relationship between the LGI3 expression level and peripheral artery disease (PAD). FIG. 8A depicts a representative correlation between incidence of aortoiliac lesion in patients and LGI3 concentration in the corresponding patient samples. FIG. 8B depicts a representative correlation between the severity of aortoiliac lesion and LGI3 concentration in the corresponding patient samples.

MODES OF THE INVENTION

Figure 2:
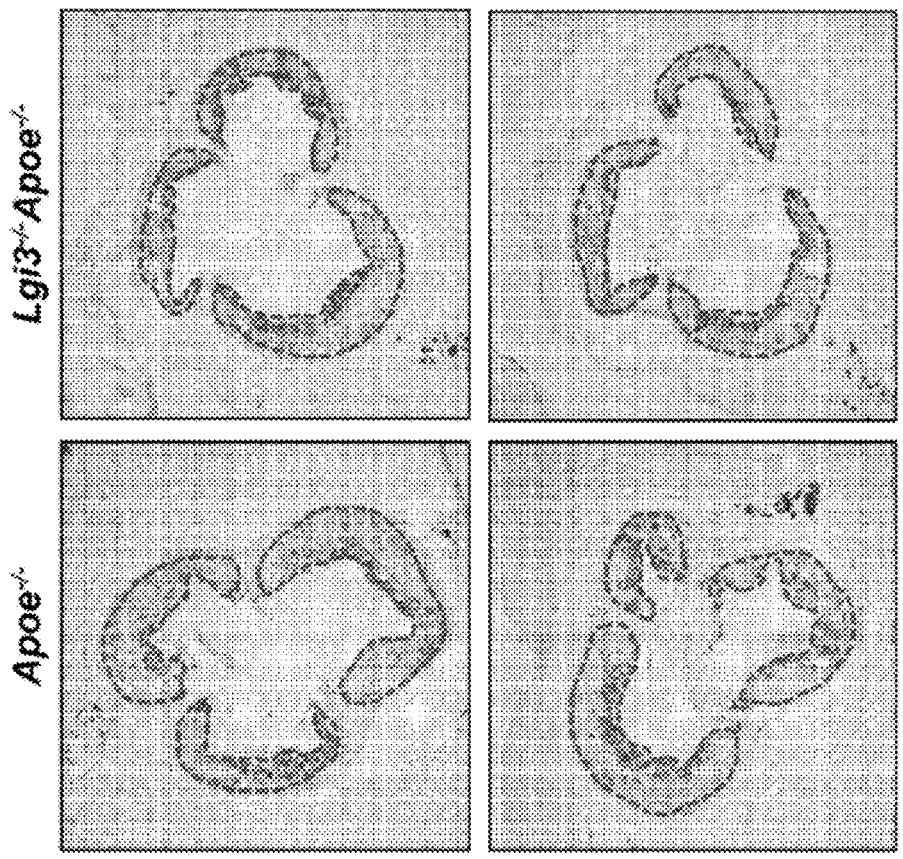
FIG. 2, comprising
Figure 2:
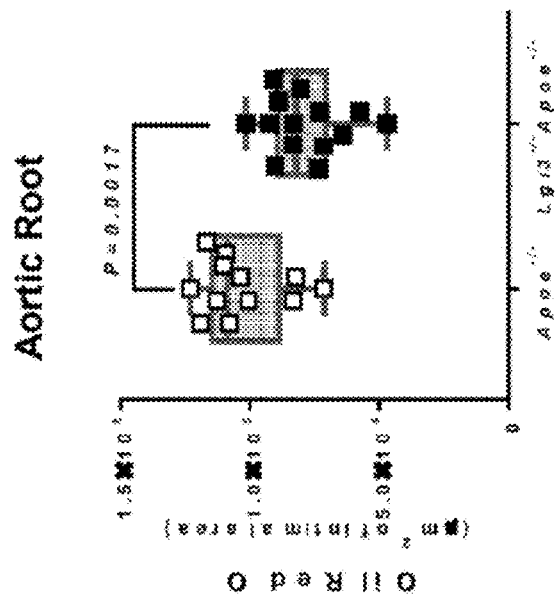

Hereinafter, preferred embodiments are presented to aid the understanding of the present invention. However, the following embodiments are provided for easier understanding of the present invention, and the contents of the present invention are not limited by the following embodiments.

The present invention relates to the use of LGI3 as a biomarker for diagnosis of arteriosclerosis severity.

More specifically, the present invention provides a biomarker composition for diagnosing the severity of atherosclerosis including LGI3 represented by the amino acid sequence of SEQ ID NO: 1 or SEQ ID NO: 3.

In addition, the present invention provides a biomarker composition for diagnosing arteriosclerosis severity, including an agent for measuring the expression or activity level of LGI3 represented by the amino acid sequence of SEQ ID NO: 1 or SEQ ID NO: 3.

In addition, the present invention provides a kit for diagnosing arteriosclerosis severity, including the composition.

In addition, the present invention provides a method of providing information for diagnosing the arteriosclerosis severity, including the steps of:
(a) checking an expression or activity level of leucine rich repeat LGI family member 3 (LGI3) represented by the amino acid sequence of SEQ ID NO: 1 or SEQ ID NO: 3 in a sample; and
(b) when the expression or activity level in the step (a) is increased compared to the expression or activity level of LGI3 represented by the amino acid sequence of SEQ ID NO: 1 or SEQ ID NO: 3 in a control group, diagnosing the arteriosclerosis severity as severe.

In the specification of the present invention, "atherosclerosis" refers to a vascular disease associated with the formation of an atheroma, and occurs frequently in the coronary arteries, the carotid arteries, the lower abdominal aorta, the popliteal artery, etc., for examples, but it is not limited thereto. The "arteriosclerosis" includes, but is not limited to, coronary artery disease or peripheral arterial disease. In addition, arrhythmia, angina, myocardial infarction, heart failure, stroke, and the like are included, but the "arteriosclerosis" is not limited thereto.

In the specification of the present invention, "coronary artery disease (CAD)" refers to a disease in which blood vessels supplying blood to the heart, especially coronary arteries, are blocked or narrowed, and thus blood is not sufficiently supplied to the heart muscle.

In the specification of the present invention, "peripheral artery disease (PAD)" refers to an obstructive disease occurring in peripheral arteries of the whole body excluding coronary arteries and aorta.

In the specification of the present invention, "angina" is a disease accompanied by symptoms of chest compression or chest pain due to a temporary lack of sufficient blood supply to the heart muscle and is one of the coronary artery diseases caused by partial narrowing of a coronary artery supplying blood to the heart. It is divided into stable angina, unstable angina, and variant angina (Prinzmetal angina). Stable angina is the main cause of arteriosclerosis, and it usually causes pain when one is exercising, overeating, emotionally anxious or excited, or when suddenly exposed to cold air after being in the house in winter. Unstable angina is a risk of heart attack as pain occurs even during rest or night sleep, or the frequency or intensity of existing chest pain gradually increases. Therefore, when unstable angina is suspected, one must be sure to consult a doctor and take appropriate measures. Variant angina is a disease in which chest pain occurs due to constriction of a coronary artery like a spasm. Chest pain occurs during nighttime sleep or at dawn, and variant angina is often asymptomatic during daytime activities, and may cause myocardial infarction and sudden death. Smoking is an important risk factor and occurs a lot in men.

In the specification of the present invention, "myocardial infarction" refers to the loss of a part of the heart muscle due to the inability of blood to pass when the blood supply to the heart is not smooth and the blood vessel is completely blocked by a thrombus or the like at some point. Often, sudden death due to heart attack is due to myocardial infarction.

In the specification of the present invention, "heart failure" refers to a state in which the pumping function of the heart is lowered, and the required amount of blood cannot be discharged to other organs of the body, and many heart diseases can cause heart failure by impairing the heart's ability to contract and relax. Heart failure usually progresses slowly over several years and the heart gradually loses its ability to pump.

In the specification of the present invention, "stroke" refers to damage to the brain caused by blood flow disorders in the brain, and is classified into hemorrhagic stroke, thrombotic stroke, and embolic stroke. Hemorrhagic stroke refers to brain damage that occurs when bleeding occurs in the brain parenchyma or between the brain and skull, the blood vessels around the hemorrhage are constricted by convulsion and blood flow to the surrounding area becomes insufficient. Thrombotic stroke occurs when blood clots in the blood vessels in the brain block blood flow, and usually occurs in an artery that is narrowed by atherosclerosis, in which fat components stick to the walls of blood vessels. Embolic stroke is caused by blood clots or small lumps that travel through blood vessels to the brain and block blood vessels in the brain, usually due to blood clots created by slow blood flow within the heart.

In the specification of the present invention, "the arteriosclerosis severity" may mean including an increase or decrease in the risk of developing arteriosclerosis, a degree of progression of a lesion, and an increase or decrease in the risk of recurrence. The degree of increase or decrease in the risk of onset is meant to include the degree of risk or possibility of developing arteriosclerosis. The degree of progression of the lesion includes a mild to severe degree of arteriosclerosis due to the onset of arteriosclerosis and the progression of the lesion. In addition, the degree of increase or decrease in the risk of recurrence is meant to include the degree of recurrence risk or the possibility of recurrence after determination of cure for arteriosclerosis. The arteriosclerosis severity may be expressed qualitatively and/or quantitatively, and the severity may be classified according to the degree.

The method of diagnosing arteriosclerosis severity according to the present invention may be used to replace a method of diagnosing severity known in the art, or may be used in combination with a method of diagnosing severity known in the art. For example, it is known in the art to measure the Synergy between PCI with Taxus and Cardiac Surgery (SYNTAX) score to diagnose the severity of coronary artery disease, and the severity of coronary artery disease is diagnosed as more severe as the SYNTAX score is higher. According to a specific example of the present invention, it was confirmed that the expression amount of LGI3 and the SYNTAX score had a direct proportional correlation. In addition, for example, it is known in the art to measure Trans-Atlantic Inter-Society Consensus (TASC) to diagnose the severity of peripheral arterial disease, and the higher the rate classified as TASC is, the more severe the severity of peripheral arterial disease is. Among the classifications of TASC in the art, it is deemed that it is increasingly serious from TASC A to TASC D. According to a specific embodiment of the present invention, it was confirmed that the expression level of LGI3 and the ratio classified as TASC had a direct proportional correlation.

In the context of the present invention, "diagnosis" means to confirm the presence or characteristics of a pathological condition. The diagnosis is meant to include not only the onset of disease, but also the prognosis, the course of arteriosclerosis, the stage, and the like. For the purposes of the present invention, diagnosis is to accurately distinguish and diagnose the arteriosclerosis severity.

In the present invention, "leucine rich repeat LGI family member 3 (LGI3)" is used as a biomarker for diagnosis of arteriosclerosis severity. The LGI3 is not limited as long as it is LGI3 of an animal having the protein, and may, for example, refer to LGI3 of a human or mouse. Preferably, the LGI3 amino acid sequence used in the present invention may be represented by the amino acid sequence of SEQ ID NO: 1 or SEQ ID NO: 3. In addition, the LGI3, which may achieve the object of the present invention, includes the whole and fragments thereof. In addition, proteins or peptides having homology to the amino acid sequence of SEQ ID NO: 1 or SEQ ID NO: 3 are included. Here, "peptide" refers to a linear molecule formed by bonding of amino acid residues to each other by peptide bonds. The LGI3-derived peptide may be obtained by fragmenting the LGI3 protein and may be prepared according to a chemical synthesis method known in the art, in particular, a solid-phase synthesis technique or a liquid-phase synthesis technique.

In the specification of the present invention, the term "biomarker" may also be used as a marker for diagnosis or a diagnostic marker and refers to a substance capable of diagnosing the arteriosclerosis severity in a sample.

For the purposes of the present invention, the biomarker for diagnosing arteriosclerosis of the present invention means that a specifically high level of expression or activity of LGI3 is shown in a sample of a patient with atherosclerosis compared to a normal control group; a specifically high level of expression or activity of LGI3 is shown in samples from patients with severe arteriosclerosis compared to samples from patients with mild arteriosclerosis; or a specifically high level of expression or activity of LGI3 is shown in a sample of a patient with a high likelihood of recurrence of atherosclerosis compared to a sample of a patient with a low probability of recurrence of atherosclerosis.

The "arteriosclerosis severity diagnostic kit" according to the present invention may include not only an agent for measuring the expression or activity level of LGI3, but also tools and reagents generally used in the art used for analysis. Examples of the tool or reagent include, but are not limited to, a suitable carrier, a labeling substance capable of generating a detectable signal, chromophores, solubilizers, detergents, buffers, stabilizers, and the like. When the labeling material is an enzyme, a substrate capable of measuring the level of enzyme activity and a reaction terminator may be included. The carrier includes a soluble carrier, an insoluble carrier, and an example of a soluble carrier includes a physiologically acceptable buffer solution known in the art, such as PBS, and an example of an insoluble carrier includes polystyrene, polyethylene, polypropylene, polyester, polyacrylonitrile, fluorine resin, cross-linked dextran, polysaccharidea, a polymer such as magnetic fine particles plated with metal on latex, different types of paper, glass, metal, agarose, and combinations thereof.

Hereinafter, each step of the method of providing information for diagnosing the arteriosclerosis severity according to the present invention will be described step by step. However, as long as the object of the present invention can be achieved, the following steps may be modified, added or replaced.

'(a) Checking an Expression or Activity Level of LGI3 (Leucine Rich Repeat LGI Family Member 3) Represented by the Amino Acid Sequence of SEQ ID NO: 1 or SEQ ID NO: 3 in a Sample'

In the specification of the present invention, "sample" refers to a tissue, blood, serum, plasma, urine or saliva, etc.

of a subject (patient) containing LGI3 for diagnosing arteriosclerosis severity, but is not limited thereto.

In the present invention, in order to confirm the expression or activity level of LGI3, an agent for measuring the expression or activity level of LGI3 is used.

The "agent for measuring the expression or activity level of LGI3" refers to a substance that can be used for detection of LGI3 by specifically binding to a protein of LGI3 or an mRNA encoding it and confirming the expression or activity level of LGI3. For example, the agent may be oligopeptides, monoclonal antibodies, polyclonal antibodies, chimeric antibodies, ligands, peptide nucleic acids (PNAs), aptamers, antisense oligonucleotides, primer pairs, probes, or the like, that specifically bind to LGI3, but is not limited thereto.

The "antibody" is a term known in the art and refers to a specific protein molecule directed against an antigenic site. For the purposes of the present invention, the antibody refers to an antibody that specifically binds to the marker of the present invention, and it can be prepared by a conventional method of cloning each gene into an expression vector and obtaining a protein encoded by the marker gene. It includes partial peptides that can be made from the protein, and the partial peptides of the present invention include at least 7 amino acids, preferably 9 amino acids, and more preferably 12 or more amino acids. The form of the antibody of the present invention is not particularly limited, and any polyclonal antibody, monoclonal antibody, or anything having antigen-binding properties is also included in the antibody of the present invention, and all immunoglobulin antibodies are included. Furthermore, the antibody of the present invention also includes special antibodies such as humanized antibodies. Antibodies used for detection of the markers of the present invention include functional fragments of antibody molecules as well as complete forms having two full-length light chains and two full-length heavy chains. The functional fragment of an antibody molecule refers to a fragment that has at least an antigen-binding function, and includes Fab, F(ab'), F(ab') 2, and Fv.

The "primer" means a nucleic acid sequence having a short free 3' hydroxyl group, which can form a complementary template and a base pair, and functions as a starting point for template strand copying. The primers can initiate DNA synthesis in the presence of a reagent for polymerization (i.e., DNA polymerase or reverse transcriptase) and four different nucleoside triphosphates in an appropriate buffer and at an appropriate temperature. In the present invention, by performing PCR amplification using the sense and antisense primers of the polynucleotide of LGI3, it may be diagnosed whether the desired product is produced. The PCR conditions, the length of the sense and antisense primers can be modified based on those known in the art.

The "probe" refers to a nucleic acid fragment such as RNA or DNA corresponding to several bases to hundreds of bases capable of specific binding to an mRNA and is labeled so that the presence or absence of a specific mRNA can be confirmed. The probe may be manufactured in the form of an oligonucleotide probe, a single stranded DNA probe, a double stranded DNA probe, an RNA probe, or the like. In the present invention, hybridization may be performed using a probe that is complementary to LGI3, and diagnosis may be performed through hybridization. Selection of suitable probes and conditions for hybridization can be modified based on those known in the art.

The primers or probes of the present invention can be chemically synthesized using the phosphoramidite solid support method, or other well-known methods. Such nucleic acid sequences can also be modified using several means known in the art. Non-limiting examples of such modifications include methylation, encapsulation, substitution of one or more homologs of natural nucleotides, and modifications between nucleotides, e.g., uncharged linkers (e.g., methyl phosphonate, phosphotriester, phosphoroamidates, carbamates, etc.) or to charged linkers (e.g., phosphorothioate, phosphorodithioate, etc.).

In the specification of the present invention, "measurement of the expression or activity level of LGI3" may be a process of confirming the presence and degree of expression or activity of the LGI3 protein or mRNA encoding the same in a sample in order to diagnose arteriosclerosis. For example, a method of determining the amount or activity level of a protein or an mRNA encoding it may be applied by using the LGI3 protein or a molecule that specifically binds to the mRNA encoding the LGI3 protein.

Methods for confirming the expression or activity level of the LGI3 protein include, for example, Western blot, enzyme linked immunosorbent assay (ELISA), radioimmunoassay (RIA), radio-immunodiffusion, Ouchterlony double immunodiffusion, rocket immunoelectrophoresis, tissue immunostaining, immunoprecipitation assay, complement fixation assay, FACS, and protein chips, and the like, but are not limited thereto. In addition, as a method of confirming the expression or activity level of the mRNA encoding the LGI3 protein, for example, reverse transcriptase polymerase reaction (RT-PCR), competitive reverse transcriptase polymerase reaction (competitive RT-PCR), real-time polymerase reaction (real time RT-PCR), real time quantitative RT-PCR, an RNase protection method, Northern blotting, gene chips, and the like, but are not limited thereto.

'(b) when the Expression or Activity Level in the Step (a) is Increased Compared to the Expression or Activity Level of LGI3 Represented by the Amino Acid Sequence of SEQ ID NO: 1 or SEQ ID NO: 3 in a Control, Diagnosing the Arteriosclerosis Severity as Severe'

In the present invention, as described above, the expression or activity level of LGI3 is checked, and when the expression or activity level of LGI3 is increased compared to the control group, the arteriosclerosis severity is diagnosed as severe.

In step (b), the term "control group" includes a normal control group other than arteriosclerosis, a sample group collected from the same patient at different times, or a sample group collected from another arteriosclerosis patient.

In the specification of the present invention, "the arteriosclerosis severity is severe" means that the arteriosclerosis severity is at an upper level.

According to the present invention, when the expression or activity level of LGI3 is increased compared to the control group, the arteriosclerosis severity is diagnosed as severe. For example, for each control group, when the expression or activity level of LGI3 in a sample of a patient with atherosclerosis is increased compared to a normal control group other than arteriosclerosis, the severity of atherosclerosis is diagnosed as severe. In addition, when the expression or activity level of LGI3 is increased in the sample group collected at the time of this method compared to the sample group collected at different times from the same patient, the arteriosclerosis severity is diagnosed as severe. Here, the term "different times" may include before starting treatment, during treatment, after treatment, after cure, and a period with the possibility of recurrence after cure of patients with atherosclerosis. In addition, when the expression or activity level of LGI3 is increased in the sample group collected during the implementation of this method compared to the sample group collected from other arteriosclerosis patients, the severity of atherosclerosis is diagnosed as severe.

In addition, the present invention provides a method of screening a substance for preventing or treating arteriosclerosis, including the following steps of:
(a) checking an expression or activity level of leucine rich repeat LGI family member 3 (LGI3) represented by the amino acid sequence of SEQ ID NO: 1 or SEQ ID NO: 3 after treatment with a candidate substance; and
(b) when the expression or activity level in step (a) is lowered, selecting the candidate substance as a material for preventing or treating arteriosclerosis.

According to this method, it is possible to appropriately select a substance for treatment or prevention according to the arteriosclerosis severity.

Hereinafter, each step of the method of screening a material for preventing or treating arteriosclerosis according to the present invention will be described step by step. However, since the present method includes the step of confirming the above-described expression or activity level of LGI3, duplicate description is omitted in order to avoid excessive complexity in the present specification. In addition, as long as the object of the present invention can be achieved, the following steps may be modified, added or replaced.

'(a) Checking an Expression or Activity Level of Leucine Rich Repeat LGI Family Member 3 (LGI3) Represented by the Amino Acid Sequence of SEQ ID NO: 1 or SEQ ID NO: 3 after Treatment with a Candidate Substance'

In the specification of the present invention, the "candidate substance" may be nucleotides, DNA, RNA, amino acids, aptamers, proteins, compounds, natural products, natural extracts, etc., and is not limited thereto as long as it can be used for preventing or treating arteriosclerosis.

'(b) when the Expression or Activity Level in Step (a) is Lowered, Selecting the Candidate Substance as a Material for Preventing or Treating Arteriosclerosis'

In the specification of the present invention, when the expression or activity level of LGI3 is lowered, it can be assumed that the arteriosclerosis severity has become mild (downward).

In the specification of the present invention, "prevention" means any action that suppresses or delays the onset of arteriosclerosis.

In the specification of the present invention, "treatment" refers to any action in which symptoms of arteriosclerosis disease are improved or beneficially changed.

In addition, the present invention provides a use for preventing, improving and/or treating arteriosclerosis including an LGI3 antagonist represented by the amino acid sequence of DEGRQKFVRFQELAV (SEQ ID NO: 3) as an active ingredient.

More specifically, the present invention provides a pharmaceutical composition for preventing or treating arteriosclerosis including an LGI3 antagonist represented by the amino acid sequence of SEQ ID NO: 3 as an active ingredient. In addition, the present invention provides a method of treating arteriosclerosis by administering an effective amount of an LGI3 antagonist represented by the amino acid sequence of SEQ ID NO: 3 to a patient with arteriosclerosis. In addition, the present invention provides a use of the LGI3 antagonist represented by the amino acid sequence of SEQ ID NO: 3 to treat or prevent arteriosclerosis.

In particular, the LGI3 antagonist according to the present invention does not affect the metabolic phenotype, and since it is only effective in treating arteriosclerosis, treatment is possible without side effects.

Before preventing and/or treating arteriosclerosis using the LGI3 antagonist represented by the amino acid sequence of SEQ ID NO: 3 according to the present invention, the step of confirming the arteriosclerotic disease or/and severity according to the present invention may be performed.

In the specification of the present invention, an "antagonist" is to be interpreted as a concept including all molecules that partially or completely block, inhibit or neutralize one or more of the biological activities of the target. The antagonist may act to reduce receptor phosphorylation, incapacitate, or kill cells that have been activated by the ligand, by binding of the receptor to the ligand. In addition, antagonists can completely disrupt the interaction between the receptor-ligand, or substantially reduce the interaction by changing the tertiary structure of the receptor, or by down regulation.

In the present invention, the pharmaceutical composition may further contain one or more substances commonly used for the prevention or treatment of arteriosclerosis while including an LGI3 antagonist as an active ingredient, and it may be formulated or used in combination with drugs such an antihistamine, an anti-inflammatory analgesic, an anti-cancer agent, and/or antibiotics.

In the present invention, the pharmaceutical composition may further include suitable carriers, excipients, and diluents commonly used in the manufacture of pharmaceutical compositions.

In the present invention, "carrier" is also called a vehicle, and refers to a compound that facilitates the addition of a compound into cells or tissues. For example, dimethyl sulfoxide (DMSO) is a commonly used carrier that facilitates the introduction of many organic compounds into cells or tissues of an organism.

In the present invention, a "diluent" is defined as a compound that is diluted in water to dissolve the compound as well as stabilize the biologically active form of the target compound. Salts dissolved in buffer solutions are used as diluents in the art. A commonly used buffer solution is phosphate buffered saline because it mimics the salt state of human solutions. Because buffer salts can control the pH of a solution at low concentrations, buffer diluents rarely alter the biological activity of a compound. The compounds used herein can be administered to a human patient as such, or as a pharmaceutical composition mixed with other ingredients, such as in combination therapy, or with suitable carriers or excipients.

In addition, the composition according to the present invention may further include one or more substances or compounds having therapeutic activity against arteriosclerosis.

In addition, the pharmaceutical composition according to the present invention may be formulated and used in the form of external preparations such as powders, granules, tablets, capsules, suspensions, emulsions, syrups, aerosols, sterile injectable solutions, and the like, respectively, according to a conventional method. Carriers, excipients, and diluents that may be included in the composition include lactose, dextrose, sucrose, oligosaccharides, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oils, and the like. In the case of formulation, the pharmaceutical composition is prepared using diluents or excipients such as fillers, extenders, binders, wetting agents, disintegrants, surfactants, and the like, that are usually used. Solid preparations for oral administration include tablets, pills, powders, granules, capsules, and the like, and these solid preparations are prepared by mixing at least one or more excipients such as starch, calcium carbonate, sucrose, lactose, or gelatin, and the like. In addition to simple excipients, lubricants such as magnesium stearate and talc are also used. Liquid preparations for oral use may include suspensions, liquid solutions, emulsions, syrups, and the like. In addition to commonly used simple diluents such as water and liquid paraffin, various excipients, such as wetting agents, sweetening agents, fragrances, preservatives, and the like, may be included. Preparations for parenteral administration may include sterilized aqueous solutions, non-aqueous solvents, suspensions, emulsions, lyophilized preparations, suppositories, and the like. As the non-aqueous solvent and suspending agent, propylene glycol, polyethylene glycol, a vegetable oil such as olive oil, and an injectable ester such as ethyl oleate may be used. As a base for suppositories, Witepsol, Macrogol, TWEEN-61® (polyoxyethylene (4) sorbitan monostearate), cacao butter, laurin butter, glycerogelatin, and the like may be used.

The preferred dosage of the pharmaceutical composition of the present invention varies depending on the condition and weight of the patient, the severity of the disease, the form of the drug, the route and duration of administration, but may be appropriately selected by those skilled in the art. Administration may be administered once a day or may be divided into several times. The above dosage does not limit the scope of the present invention in any way. In addition, an effective amount for single administration may be formulated as a single formulation in a unit dosage form, formulated in an appropriate amount, or prepared by incorporating into a multi-dose container.

The pharmaceutical composition according to the present invention may be administered to mammals such as rats, mice, livestock, humans, and the like, by various routes such as parenteral and oral administration, and all modes of administration can be expected and the pharmaceutical composition may be administered, for example, by oral, rectal, or intravenous, intramuscular, subcutaneous, intrauterine dura mater or intracerebroventricular injection etc. However, when administered orally, since the protein or peptide is digested, the oral composition should be coated with an active agent or formulated to be protected from degradation in the stomach. Preferably, it may be administered to the descending thoracic aorta. Alternatively, the composition may be administered by any device capable of moving the active substance to the target cell.

In addition, the oral dosage form may vary depending on the patient's age, sex, and weight, but an amount of 0.1 to 100 mg/kg may be administered once to several times a day. In addition, the dosage may be increased or decreased according to the route of administration, the degree of disease, sex, weight, age, and the like. Therefore, the above dosage does not limit the scope of the present invention in any way.

In the present invention, when provided as a mixture in which components other than the LGI3 antagonist are added, the composition may contain 0.001 wt % to 99.9 wt %, preferably 0.1 wt % to 99.0 wt %, more preferably, 30 wt % to 50 wt % of the LGI3 antagonist based on the total weight of the composition.

The present invention provides a food composition for preventing or improving arteriosclerosis, including an LGI3 antagonist as an active ingredient. In addition, the LGI3 antagonist may be added to food for the purpose of improving arteriosclerosis or a vascular disease. When the LGI3 antagonist of the present invention is used as a food additive, the LGI3 antagonist may be added as it is or may be used with other foods or food ingredients and may be appropriately used according to a conventional method. However, when administered orally as food, since proteins or peptides are digested, the oral composition should be coated with an active agent or formulated to be protected from degradation in the stomach. The mixing amount of the active ingredient may be appropriately determined according to the purpose of use (prevention, health, or therapeutic treatment). In general, in the manufacture of food or beverages, the LGI3 antagonist of the present invention is added in an amount of 15 wt % or less, preferably 10 wt % or less of the raw material. However, in the case of long-term intake for the purpose of health and hygiene or for the purpose of health control, the amount may be below the above range, and there is no problem in terms of safety, so the active ingredient may be used in an amount above the above range.

In the present invention, food includes functional foods and health functional foods, and the term "functional food" refers to food in which the functionality of general foods is improved by adding the LGI3 antagonist (azelaic acid) of the present invention to general foods. Functional properties may be broadly classified into physical properties and physiological functions. When the LGI3 antagonist (azelaic acid) of the present invention is added to general foods, the physical properties and physiological functions of general foods may be improved, and the present invention comprehensively defines such a food with improved function as a "functional food".

The functional food of the present invention may be used in various ways such as drugs, foods, and beverages for preventing or improving arteriosclerosis. There is no particular limitation on the type of food. Examples of foods to which the substance can be added include meat, sausage, bread, chocolate, candies, snacks, confectioneries, pizza, ramen, other noodles, gums, dairy products including ice cream, various soups, beverages, tea, drinks, alcoholic beverages and vitamin complexes, and all foods in the usual sense are included.

The health beverage composition according to the present invention may contain various flavoring agents or natural carbohydrates as an additional component, like a conventional beverage. The natural carbohydrates described above are monosaccharides such as glucose and fructose, disaccharides such as maltose and sucrose, polysaccharides such as dextrin and cyclodextrin, and sugar alcohols such as xylitol, sorbitol and erythritol, etc. As the sweetener, natural sweeteners such as thaumatin and stevia extract, and synthetic sweeteners such as saccharin and aspartame may be used. The proportion of the natural carbohydrate is generally about 0.01-20 g, preferably about 5-12 g per 100 mL of the composition of the present invention.

In addition to the above, the composition of the present invention may include various nutrients, vitamins, electrolytes, flavoring agents, colorants, pectic acid and salts thereof, alginic acid and salts thereof, organic acids, protective colloidal thickeners, pH adjusters, stabilizers, preservatives, glycerin, alcohols, carbonating agents, and the like used in carbonated beverages. In addition, the composition of the present invention may contain flesh to produce natural fruit juices, fruit juice beverages, and vegetable beverages. These components may be used independently or in combination. Although the proportion of these additives is not important, it is generally selected in the range of 0.01-0.20 parts by weight per 100 parts by weight of the composition of the present invention.

Since various modification may be applied to the present invention and thus the present invention has various embodiments, specific embodiments are illustrated in the drawings and will be described in detail in the detailed description. However, this is not intended to limit the present invention to a specific embodiment, it should be understood to include all conversions, equivalents, and substitutes included in the spirit and scope of the present invention. In describing the present invention, when it is determined that a detailed description of related known technology may obscure the subject matter of the present invention, a detailed description thereof will be omitted.

EXAMPLES AND EXPERIMENTAL EXAMPLES

Example 1

Example 1-1. Experimental Animals

Lgi3 knockout mice made by Macrogen (Korea) were donated by Dr. Hye-Young Yun (Chung-ang University, Korea). Lgi3−/− somatic cells were recrossed for more than 10 generations with C57Bl/6 as the background, and the mice were confirmed to have no serious abnormalities in the weight of the spleen and thymus or other hematologic parameters. A B6.129P2-Apoetm1Unc/J (JAX stock #002052, Apoe −/−) mouse strain was purchased from Jackson Laboratory. Lgi3 −/− mice were crossed with Apoe −/− mice to create Lgi3 −/− Apoe −/− mice. Lgi3 −/− Apoe −/− mice and congenic Apoe −/− mice fed a high-fat, high-cholesterol diet for 16 weeks was used as controls.

Example 1-2. Plaque Formation Test

Plaque formation was induced in male littermates (8 weeks old, n=13 to 15) by a high fat diet for 16 weeks. Briefly, after euthanizing mice with $CO_2$, the right atrium was removed, and the atrium and aorta were perfused with phosphate buffered saline (PBS) through the left ventricle. Hearths were inserted into an OCT compound (Sakura, USA) and frozen at −80° C. The aorta was dissected from the proximal ascending aorta to the iliac artery bifurcation, and fat from the adventitia was removed. For en face analysis, the aorta was opened longitudinally and fixed with 10% neutral buffered formaldehyde in PBS overnight on a flat black silicone plate. The fixed aorta was stained with Oil Red O overnight, washed with PBS, and photographed digitally at a fixed magnification. Total aortic area and lesion area were calculated using Axio Vision (Carl Zeiss, Germany).

Example 1-3. Immunoblotting and ELISA

Mouse plasma was measured with a commercially available ELISA kit (LGI3 (CUSABIO CSB-EL012900MO)) according to the manufacturer's instructions.

Example 1-4. Mouse LGI3 Antagonist Peptide (LGI3 P34) Injection

LGI3 P34, made with a mouse LGI3 antagonist peptide, is a 15mer synthetic peptide containing amino acids (aa) 1 to 34 (DEGRQKFVRFQELAV (SEQ ID NO:3)) of mouse Lgi3. The synthetic LGI3 peptide was dissolved in PBS and sterilized by filtration. PBS injection was used as a control for mouse experiments. All peptides were synthesized by Peptron (Seoul, Korea). Apoe$^{-/-}$ mice fed a high fat diet for 16 weeks were intraperitoneally injected with PBS or the LGI3 antagonist peptide twice a week for the last 5 weeks.

Example 1-5. Statistical Analysis

Statistical analysis was performed using InStat. A two-sided Mann-Whitney U-test was used for comparison between two groups, and one-way ANOVA was used for comparisons among three or more groups. All data is presented as mean s.e.m, and P-values of ≤0.05 were considered statistically significant.

Example 2

Example 2-1. Research Group

This study included a total of 68 patients from the Yonsei University Cardiovascular Genome Center database. Patients were enrolled when they underwent coronary angiography for their chest pain, and when they underwent coronary angiography, they were given a screening test or peripheral angiography for claudication of the lower extremities (pain that occurs during exercise) or for pain at rest. Subjects aged 30 to 70 years with at least 50% or more stenosis in at least one epicardial coronary artery were included.

Example 2-2. Clinical and Angiographic Data Collection

At the time of enrollment, subjects were interviewed for their individual medical history and underwent a complete physical examination. Hypertension was defined as blood pressure >140/90 mmHg at two or more times or receiving antihypertensive therapy. Diabetes was defined as fasting blood glucose ≥126 mg/dL, postprandial blood glucose ≥200 mg/dL, or currently receiving hypoglycemic medication. Hyperlipidemia was defined as low-density lipoprotein cholesterol ≥160 mg/dL. Coronary angiography and peripheral angiography were reviewed to evaluate coronary artery disease (CAD) and peripheral arterial disease (PAD) characteristics by a cardiologist who was unaware of the purpose of the study (blinded). The cardiologist initially assessed the clinical manifestation of the most severe CAD in the patient's medical history, and then the number of coronary arteries with stenosis of at least 50% or more. To assess the severity and degree of CAD, a SYNTAX (PCI with Taxus and Cardiac Surgery) score was determined. The presence of PAD was defined as the presence of at least 50% or more of a stenosis site at the level of the aorta to the iliac artery, and the severity was determined according to the definition of Trans-Atlantic Inter-Society Consensus (TASC) II.

Example 2-3. ELISA for Determination of LGI3 Levels in Human Serum

Data on common chemistry and other cardiovascular markers were obtained from the database of the Cardiovascular Genomic Center. For the measurement of LGI3 levels, venous samples collected after a 12-hour fasting period were used. These samples were collected at the time of subject enrollment, centrifuged, and stored at −80° C. For ELISA analysis, human serum samples were measured using a commercially available ELISA kit LGI3 (CUSABIO CSB-EL012900HU), ADIPONECTIN (R&D Systems DRP300) according to the manufacturer's instructions. 96-well plates were coated with 1 mg/well of a capture antibody using an ELISA kit (Cusabio Biotech Corporation, USA). The coated plate was washed with PBS containing 0.05% TWEEN-20® (polysorbate 20), incubated with a culture medium, and then incubated with a biotin-conjugated secondary antibody. The plate was read at an absorbance of 450 nm. The target protein was analyzed according to the manufacturer's specifications. Appropriate specificity controls were included, and all samples were analyzed in duplicate.

Example 2-4. Clinical Follow-Up Observation

Clinical follow-up was assessed through a review of post-discharge medical records conducted at the clinical visit. The clinical event was defined according to the Academic Research Consortium and an expert consensus document defining a third universal definition of myocardial infarction. When no apparent non-cardiac cause was identified, all deaths were considered heart related. After discharge from a hospital, myocardial infarction is defined by the presence or absence of clinical symptoms, changes in an electrocardiogram, or abnormal imaging findings indicating myocardial infarction, and when the creatine kinase myocardial band fraction exceeds the upper limit of a normal value, or when troponin-T/troponin-I exceeds the 99th percentile of an upper limit. Stroke was confirmed by a neurologist based on radiological studies, as indicated by neurological deficits. A major adverse cardiac and cerebrovascular event (MACCE) was defined as a combination of heart death, stroke, and myocardial infarction.

Experimental Example 1

Experimental Example 1-1. Lgi3 Deficiency Improved Atherosclerotic Plaque Formation (FIG. 1)

To investigate the effect of the Lgi3 deletion effect on atherosclerotic plaque, mice were fed a high fat diet for 16 weeks and then plaque formation was analyzed. Lgi3 −/− Apoe −/− mice showed reduced plaque formation across the aorta compared to Apoe −/− mice (19.7±2.17, n=13 vs. 13.34±1.26, n=15; %, P=0.0008). In addition, significantly reduced plaque formation was seen in the ascending aorta and arch, abdominal aorta, and especially the descending thoracic aorta when Lgi3 is deficient.

Experimental Example 1-2. Lgi3 Deficiency Improved the Formation of Lesions in the Aorta (FIG. 2)

The mean lesion area of Lgi3 −/− Apoe−/− mice in the aortic sinus was significantly lower than that of control mice (103,484.9±15,558.77, n=12 vs. 78,329.36±14,425.65, n=14; μm², P=0.0017).

Figure 3:
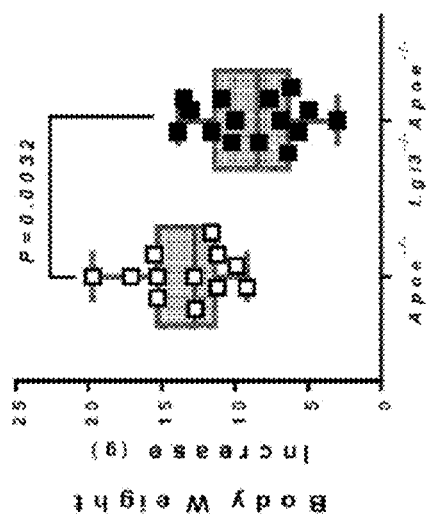
FIG. 3, comprising
Figure 3:
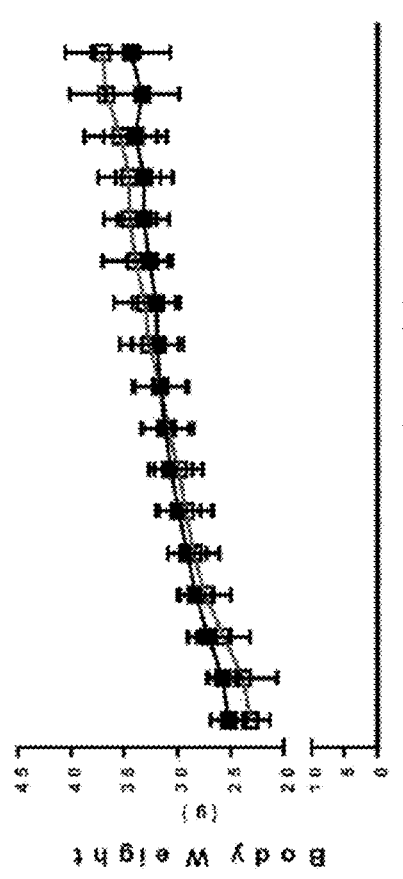
Figure 3:
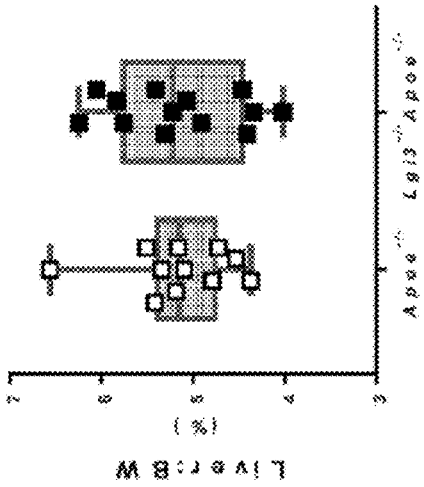
Figure 3:
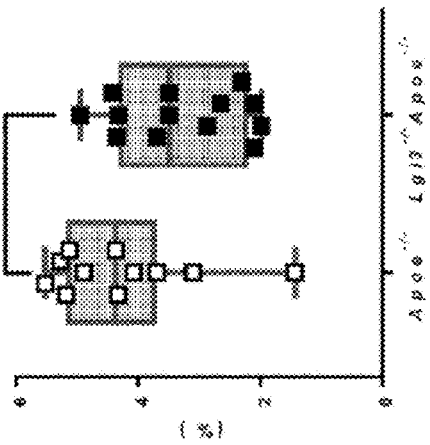

Experimental Example 1-3. The Effect of Lgi3 on the Pathogenesis of Atherosclerosis was Confirmed (FIG. 3)

In this study, to investigate the effect of Lgi3 on the pathogenesis of atherosclerosis, Lgi3 −/− Apoe−/− were created with Apoe−/− littermate control. During the diet from 8 weeks of age to 16 weeks, the change in body weight was smaller in Apoe−/− mice deficient in Lgi3. More interestingly, in the case of Lgi3 −/− Apoe−/−, after ingesting a high fat diet for 16 weeks, the fat weight of the inguinal region was further reduced, along with a reduced weight gain rate compared to the control group. This data suggests that Lgi3 deficiency during the onset of atherosclerosis represents a phenotype of reduced susceptibility to disease.

Figure 4:
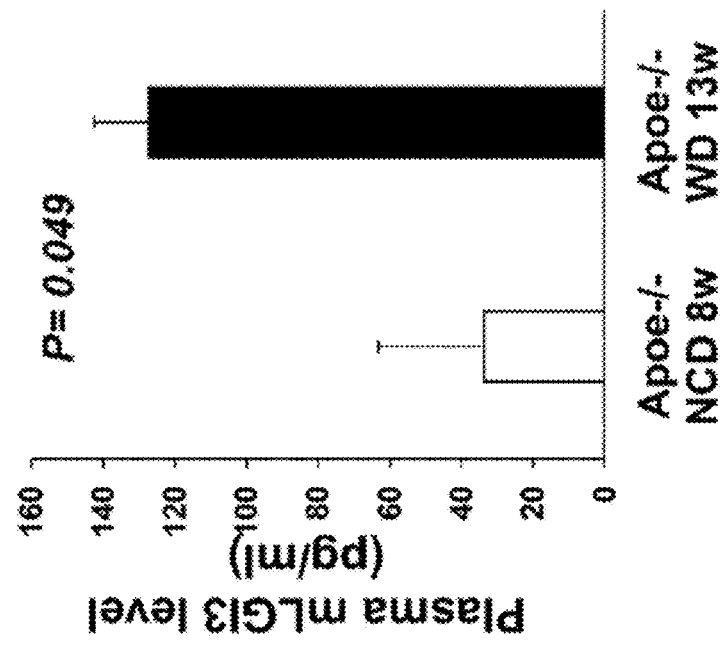
FIG. 4, comprising

Experimental Example 1-4. LGI3 was Increased in Plasma of a Mouse Model of Atherosclerosis (FIG. 4)

LGI3 is a soluble form proposed as being the form of adipokines and is mainly known as a 60 kDa protein. It has been reported that LGI3 negatively regulates adiponectin and has a positive correlation with tumor necrosis factor-α (TNF-α). TNF-α is a well-known inflammatory adipokine, and adiponectin is known as a representative anti-inflammatory adipokine. Recently, adipokines released from perivascular adipose tissue have been reported to affect hyperlipidemia-causing diseases such as atherosclerosis. However, the physiological or pathological relationship between LGI3 and atherosclerosis is unknown. Because LGI3 expression was increased in the white adipose tissue (WAT) of atherosclerotic mice, when assessing plasma LGI3 levels in Apoe deficient (Apoe −/−) mice, it was secreted from WAT and appeared to have a positive correlation with severity. Apoe −/− mice fed a high fat diet for 13 weeks showed higher plasma LGI3 levels compared to the 8-week Apoe −/− control mice (127.31±15.19; n=4; versus 33.8±29.42; n=5, pg/ml, P=0.049). In addition, plasma LGI3 levels of mice were significantly increased in the plasma of Apoe −/− mice with an atherosclerotic aorta during the onset of intermediate atherosclerosis without a hyperlipidemia diet. This data showed that LGI3 plays an important role in atherosclerosis, and that LGI3 is a biomarker in mouse atherosclerosis.

Experimental Example 1-5. LGI3 Antagonist Reduced Atherosclerotic Plaque Formation in Apoe −/− Mice (FIG. 5)

The above data demonstrates that LGI3 is a new biomarker in chronic inflammatory diseases, especially atherosclerosis. It is assumed that LGI3 is secreted from WAT when atherosclerotic conditions are induced and it promotes pro-inflammatory signaling through an unknown mechanism that can be mediated by receptors, ADAM22 or ADAM23. To confirm the effect of LGI3 inhibition and to test the possibility of developing it as a therapeutic target, PBS or the LGI3 antagonist peptide was injected intraperitoneally into Apoe −/− mice for 5 weeks on a high fat diet for 16 weeks. Interestingly, the LGI3 antagonist peptide-injected group showed reduced plaque formation compared to the control group (11.42±0.97; n=9 vs. 14.76±1.26; n=9; %, P=0.04). In particular, plaque formation was significantly reduced in the descending thoracic aorta after treatment with an LGI3 antagonist (4.44±0.58; n=9 vs. 7.52±1.26; n=9; %, P=0.01), suggesting that LGI3 may be involved in this reduction. Receptor ADAM23 is expressed by perivascular adipose tissue located right next to the aorta, and this data also demonstrates that LGI3 inhibition may be developed as a therapeutic strategy to treat atherosclerosis.

Experimental Example 1-6. The LGI3 Antagonist Showed a Plaque Reduction Effect without Altering the Metabolic Phenotype (FIG. 6)

The above data showed that there is no difference between the PBS-injected group and the LGI3 antagonist-injected group in body weight and other major metabolic organ weights, especially epididymal fat weight (39.22±3.51; n=9 vs. 38.08±2.19; n=9; g, P=0.536±1.689±0.43; n=9 vs. 1.58±0.51; n=9; %, P=0.84). This data suggested that the effect of the LGI3 antagonist peptide dominates the formation of atherosclerotic plaque, not reducing fat or alleviating obesity. In addition, this data indicated that the LGI3 antagonist peptide could improve atherosclerosis and be used as a therapeutic agent for atherosclerosis without altering metabolic parameters.

Experimental Example 2

The mean level of LGI3 was 13.04±8.03 ng/mL, and patients were classified as follows according to the quartile of the LGI3 level: Q1 (n=17) 4.34±1.58 ng/mL; Q2 (n=17) 9.79±1.53 ng/mL; Q3 (n=17) 14.19±1.82 ng/mL; and Q4 (n=17) 23.85±6.96 ng/mL. The clinical and test results according to the quartile of the LGI3 level are shown in Table 1. Although not statistically significant, BMI was lower in the fourth quartile of the LGI3 level (P=0.083). Also, the level of creatine and hsCRP were higher in the fourth quartile of the LGI3 level.

The SYNTAX score gradually increased according to the quartile of the LGI3 level and was highest when the SYNTAX score was 25.9±14.3 in the fourth quartile of the LGI3 level (P<0.001) (left side of FIG. 7). In addition, when the LGI3 level was treated as a continuous variable, it was found that there was a positive correlation between the LGI3 level and the SYNTANX score (R2=0.419, P<0.001) (right side of FIG. 7).

In addition, a high LGI3 level was found to be associated with the severity and the degree of CAD. In addition to the severity of CAD, the frequency of PAD also gradually increased according to the quartile of the LGI3 level, such as 5.9%, 5.9%, 11.8%, and 29.4% (FIG. 8). The degree of angiography of PAD as defined by the TASC II classification was significantly more severe according to the fourth quartile of the LGI3 level (P=0.036) (FIG. 8).

Figure 9:
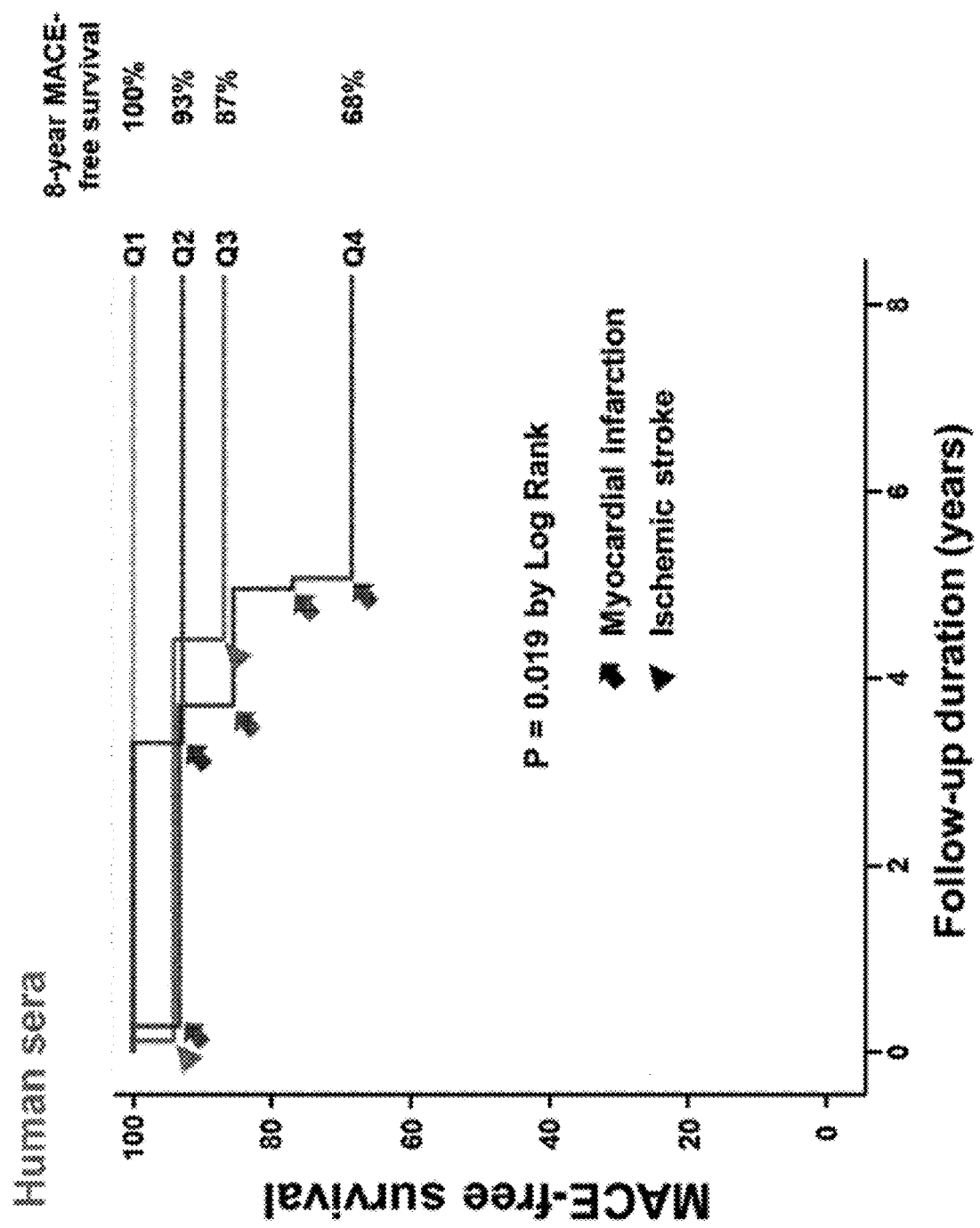
FIG. 9 shows the relationship between LGI3 expression levels and major adverse cardiac and cerebrovascular events (MACCE) risk factors.

During the median follow-up period for 5.7 years (interquartile range is 3.9 to 10.1 years), there was no myocardial infarction or stroke in patients in the first quartile of the LGI3 level, but there was acute myocardial infarction in patients in the second quartile of the LGI3 level. There were strokes in the third quartile of LGI3 level and acute myocardial infarction in the fourth quartile of LGI3 level. Therefore, the MACCE survival rates for 8 years were 100%, 93%, 87%, and 68%, respectively (FIG. 9), suggesting that the higher the level of LGI3, the higher the frequency of heart and cerebrovascular diseases.

The above description of the present invention is for illustrative purposes only, and those of ordinary skill in the art to which the present invention pertains will be able to understand that it is possible to easily modify the present invention into other specific forms without changing the technical idea or essential features of the present invention. Therefore, it is to be understood that the embodiments described above are illustrative and non-limiting in all respects.

TABLE 1

|  | Q1 | Q2 | Q3 | Q4 | P-value |
| --- | --- | --- | --- | --- | --- |
| Lgi3 | 4.34 ± 1.58 | 9.79 ± 1.53 | 14.19 ± 1.82 | 23.85 ± 6.96 | <0.001 |
| Adiponectin | 6.51 ± 9.19 | 6.80 ± 4.78 | 7.78 ± 8.40 | 3.28 ± 2.04 | 0.72 |
| Age | 67 ± 5 | 67 ± 4 | 67 ± 11 | 68 ± 7 | 0.948 |
| Men | 11 (65%) | 10 (59%) | 6 (35%) | 12 (71%) | 0.173 |
| Height | 162 ± 9 | 162 ± 7 | 159 ± 7 | 164 ± 8 | 0.241 |
| Weight | 66 ± 13 | 62 ± 11 | 63 ± 9 | 61 ± 8 | 0.568 |
| BMI | 25.1 ± 3.6 | 23.5 ± 2.9 | 24.9 ± 2.8 | 22.8 ± 2.6 | 0.083 |
| WBC | 7210 ± 1812 | 7479 ± 3425 | 6958 ± 1990 | 7933 ± 5023 | 0.861 |
| Hemoglobin | 13.1 ± 1.7 | 13.1 ± 1.3 | 13.3 ± 1.6 | 11.9 ± 2.1 | 0.066 |
| Platelet | 237 ± 53 | 277 ± 79 | 236 ± 69 | 251 ± 85 | 0.337 |
| Glucose | 145 ± 94 | 106 ± 22 | 123 ± 43 | 136 ± 76 | 0.268 |
| BUN | 15.9 ± 5.5 | 16.8 ± 7.0 | 17.1 ± 2.7 | 20.2 ± 9.1 | 0.253 |
| Cr | 1.02 ± 0.32 | 0.98 ± 1.20 | 0.88 ± 0.18 | 1.90 ± 2.30 | 0.052 |
| Cholesterol | 160 ± 35 | 172 ± 35 | 153 ± 46 | 164 ± 50 | 0.638 |
| Triglyceride | 118 ± 46 | 143 ± 74 | 119 ± 42 | 110 ± 63 | 0.387 |
| HDL-cholesterol | 44.35 ± 11.01 | 44.65 ± 14.45 | 44.25 ± 11.35 | 41.76 ± 11.73 | 0.894 |
| LDL-cholesterol | 104.3 ± 34.7 | 110.2 ± 33.6 | 92.6 ± 41.4 | 101.0 ± 41.6 | 0.607 |
| Free fatty acid | 404.7 ± 279.8 | 434.5 ± 384.5 | 530.8 ± 423 1 | 714.9 ± 422.3 | 0.271 |
| Lipoprotein(a) | 28.6 ± 16.9 | 21.7 ± 18.7 | 20.5 ± 17.7 | 35.4 ± 30.5 | 0.348 |
| hsCRP | 5.06 ± 10.8 | 16.98 ± 49.2 | 5.24 ± 10.45 | 36.5 ± 57.7 | 0.088 |
| Homocystein | 14.4 ± 7.6 | 12.6 ± 3.6 | 10.8 ± 3.9 | 15.0 ± 6.1 | 0.361 |
| SYNTAX score | 8.3 ± 5.7 | 9.7 ± 8.7 | 12.5 ± 12.4 | 25.9 ± 14.3 | 0.001 |

INDUSTRIAL APPLICABILITY

According to the present invention, it is possible to develop a therapeutic substance for improving the arteriosclerosis severity, and the present invention is expected to provide a platform for using the therapeutic substance in various ways, such as pharmaceutical, external, or food additive compositions. Furthermore, according to the present invention, since the metabolic phenotype is not affected, it is expected that atherosclerosis treatment is possible without side effects.

```
                    Sequence List Free Text

SEQ ID NO. 1 (leucine rich repeat LGI family member 3)
Length: 548
Type: Protein
Organism: Homo sapiens
Sequence:
  1 maglrarggp gpgllalsal gfclmlqvsa krppktppcp pscsctrdta fcvdskavpr
 61 nlpsevislt lvnaafseiq dgafshlpll qflllnsnkf tligdnaftg lshlqylfie
121 nndiwalskf tfrglkslth lslannnlqt lprdifrpld ilndldlrgn slncdckvkw
181 lvewlahtnt tvapiycasp prfqehkvqd lplrefdcit tdfvlyqtla fpaysaepfl
241 yssdlylala qpgvsactil kwdyverqlr dydripapsa vhckpmvvds qlyvvvaqlf
301 ggsyiyhwdp nttrftrlqd idpqrvrkpn dleafridgd wyfavadssk agatslyrwh
361 qngfyshqal hpwhrdtdle fvdgegkprl ivssssqapv iyqwsrtqkq fvaggevtqv
421 pdaqavkhfr agrdsylcls ryigdskilr wegtrfsevq alpsrgslal qpflvggrry
481 lalgsdfsft qiyqwdegrq kfyrfqelay qaprafcymp agdaqlllap sfkgqtlvyr
541 hivvdlsa SEQ ID NO. 2 (leucine rich repeat LGI family member 3)
Length: 548
Type: Protein
Organism: Mus musculus
Sequence:
  1 maglrarrgp grrllvlstl gfclmlqvsa krppktppcp pscsctrdta fcvdsksvpk
 61 nlpsevislt lvnaafseiq dgafshlpll qflllnsnkf tligdnafig lshlqylfie
121 nndiwalskf tfrglkslth lslannnlqt lprdifrpld ilsdldlrgn alncdckvkw
181 lvewlahtnt tvapiycasp prfqehkvqd lplrefdcit tdfvlyqtls fpaysaepfl
241 yssdlylala qpgasactil kwdyverqlr dydripapsa vhckpmvvdg qlyvvvaqlf
301 ggsyiyhwdp nttrftklqd idpqrvrkpn dleafridgd wffavadssk agatslyrwh
361 qngfyshqal hawhrdtdle fvdgegkprl ivssssqapv iyqwsrsqkq fvaqgevtqv
421 pdaqavkhfr agrdsylcls ryigdskilr wegtrfsevq alpsrgslal qpflvgghry
481 lalgsdfsft qiyqwdegrq kfvrfqelav qaprafcymp agdaqlllap sfkgqtlvyr
541 hvvvdlsa SEQ ID NO. 3 (leucine rich repeat LGI family member 3)
Length: 15
Type: Protein
Organism: Homo sapiens
Sequence: DEGRQKFVRFQELAV
```

The invention claimed is:

1. A method for reducing plaque formation in a subject in need thereof, comprising the steps of:
   (a) measuring the expression of leucine rich repeat LGI3 family member 3 (LGI3) comprising the amino acid sequence of SEQ ID NO: 1 in a subject sample comprising tissue, blood, serum, plasma, urine or saliva;
   (b) diagnosing the subject as having severe arteriosclerosis, wherein an increase in expression of LGI3 comprising the amino acid sequence of SEQ ID NO:1 in comparison to the expression of LGI3 in a control group diagnoses the subject with severe arteriosclerosis, and wherein the average LGI3 expression of the control group is 4.34 ng/mL or less in a sample comprising tissue, blood, serum, plasma, urine, or saliva; and
   (c) administering to the subject with severe arteriosclerosis a pharmaceutical composition comprising a peptide consisting of the amino acid sequence of DEGRQKFVRFQELAV (SEQ ID NO:3).

2. The method of claim 1, wherein the severe arteriosclerosis is coronary artery disease (CAD) or peripheral artery disease (PAD).

3. The method of claim 1, wherein the step (b) further comprises diagnosing the subject with a low major adverse cardiac and cerebrovascular event (MACCE)-free survival rate in the subject with severe arteriosclerosis, wherein an increase in the expression level of LGI3 comprising the amino acid sequence of SEQ ID NO:1 in comparison to the control group diagnoses the subject with severe arteriosclerosis with a low MACCE-free survival rate, and wherein the average LGI3 expression of the control group is 4.34 ng/mL or less in a sample comprising tissue, blood, serum, plasma, urine, or saliva.

4. The method of claim 3, wherein the major adverse cardiac and cerebrovascular event is a myocardial infarction or a stroke.

5. The method of claim 2, wherein step (b) further comprises measuring a Synergy between PCI (percutaneous coronary intervention) with Taxus and Cardiac Surgery (SYNTAX) score for the subject in diagnosing a severity of CAD.

6. The method of claim 2, wherein step (b) further comprises determining a Trans-Atlantic Inter-Society Consensus (TASC) classification for the subject in diagnosing a severity of PAD.

* * * * *